US005461047A

United States Patent [19]
Hansen, Jr. et al.

[11] Patent Number: 5,461,047
[45] Date of Patent: * Oct. 24, 1995

[54] 2-,3-,4-,5-,6-,7-,8-,9- AND/OR 10-SUBSTITUTED DIBENZOXAZEPINE AND DIBENZTHIAZEPINE COMPOUNDS, PHARMACEUTICAL COMPOSITIONS AND METHODS OF USE

[75] Inventors: Donald W. Hansen, Jr., Skokie; Karen B. Peterson, Vernon Hills, both of Ill.

[73] Assignee: G. D. Searle & Co., Chicago, Ill.

[*] Notice: The portion of the term of this patent subsequent to Oct. 11, 2011 has been disclaimed.

[21] Appl. No.: 245,349

[22] Filed: May 18, 1994

Related U.S. Application Data

[63] Continuation-in-part of Ser. No. 79,021, Jun. 16, 1993, Pat. No. 5,354,747.

[51] Int. Cl.$^6$ ............... C07D 413/06; C07D 417/06; A61K 31/55
[52] U.S. Cl. ............................. 514/211; 540/547
[58] Field of Search ............... 540/547; 514/211

[56] References Cited

U.S. PATENT DOCUMENTS

| | | | |
|---|---|---|---|
| 2,852,528 | 9/1958 | Hoffman | 260/327 |
| 3,210,372 | 10/1965 | Harvey | 260/309.6 |
| 3,258,459 | 6/1966 | Yale et al. | 260/243 |
| 3,357,998 | 12/1967 | Cusic et al. | 260/333 |
| 3,419,554 | 12/1968 | Bernstein | 260/243 |
| 3,452,046 | 6/1969 | Yale et al. | 260/327 |
| 3,534,019 | 10/1970 | Coyne et al. | 260/239 |
| 3,624,104 | 11/1971 | Cusic et al. | 260/333 |
| 3,644,346 | 2/1972 | Cusic et al. | 260/240 |
| 3,917,649 | 11/1975 | Mueller et al. | 260/333 |
| 3,989,719 | 11/1976 | Mueller et al. | 260/333 |
| 3,992,375 | 11/1976 | Mueller et al. | 260/240 |
| 4,045,442 | 8/1977 | Mueller et al. | 260/293.58 |
| 4,125,532 | 11/1978 | Mueller et al. | 260/244 |
| 4,170,593 | 10/1979 | Mueller et al. | 260/243.3 |
| 4,221,715 | 9/1980 | McKenzie | 260/244.4 |
| 4,290,953 | 9/1981 | Koizumi | 260/333 |
| 4,360,525 | 11/1982 | Mueller et al. | 424/267 |
| 4,379,150 | 4/1983 | Ito | 424/244 |
| 4,434,171 | 2/1984 | Mueller et al. | 424/267 |
| 4,559,336 | 12/1985 | Mueller et al. | 514/211 |
| 4,559,337 | 12/1985 | Mueller et al. | 514/211 |
| 4,614,617 | 9/1986 | Mueller et al. | 540/547 |
| 4,681,939 | 7/1987 | Mueller et al. | 540/547 |
| 4,704,386 | 11/1987 | Mueller et al. | 514/211 |
| 5,180,720 | 1/1993 | Husa et al. | 514/211 |
| 5,182,272 | 1/1993 | Hallinan et al. | 514/80 |
| 5,212,169 | 5/1993 | Husa et al. | 514/211 |
| 5,225,417 | 7/1993 | Dappen et al. | 514/279 |
| 5,281,590 | 1/1994 | Husa et al. | 514/211 |
| 5,283,240 | 2/1994 | Hallinan et al. | 514/80 |
| 5,288,719 | 2/1994 | Husa et al. | 514/211 |
| 5,304,644 | 4/1994 | Husa et al. | 540/547 |
| 5,354,747 | 10/1994 | Hansen, Jr. et al. | 514/211 |

FOREIGN PATENT DOCUMENTS

| | | | |
|---|---|---|---|
| 2056874A1 | 12/1991 | Canada | C07D 295/16 |
| 0012385 | 6/1980 | European Pat. Off. | C09D 267/20 |
| 0193822 | 9/1986 | European Pat. Off. | C07D 267/20 |
| 0218077 | 4/1987 | European Pat. Off. | C07D 267/20 |
| 0480641A1 | 4/1992 | European Pat. Off. | C07D 223/20 |
| 0534667A1 | 3/1993 | European Pat. Off. | C07D 417/06 |
| 1161339 | 8/1958 | France . | |
| 4041465A1 | 6/1990 | Germany | A61K 31/645 |
| 6700603 | 7/1967 | Netherlands . | |
| 648309A5 | 3/1985 | Switzerland | C07D 401/04 |
| 1170322 | 4/1969 | United Kingdom | C07D 87/54 |
| 1331892 | 9/1973 | United Kingdom | C07D 87/54 |
| 1522003 | 8/1978 | United Kingdom | C07I 267/20 |
| WO92/19617 | 11/1992 | WIPO | C07D 413/12 |
| WO93/07132 | 4/1993 | WIPO | C07D 267/20 |
| WO93/09104 | 5/1993 | WIPO | C07D 267/20 |

OTHER PUBLICATIONS

Jilek et al, Chemical Abstract 62:14707h–14708a (1964).
Mach et al, Chemical Abstract 52:4652i (1957).
A. Bennett, et al. "Antagonism of Prostanoid–Induced Contractions of Rat Gastric Fundus Muscle by Sc–19220 Sodium Meclofenamate, Indomethacin or Trimethoquinol," *Br. J. Pharmac.*, 71, 169–175 (1980)–London.
W. E. Coyne, et al. "Anticonvulsant Semicarbazides," *J. Med. Chem.*, 11(6), 1158–1160 (1968)–USA.
E. J. Drower, et al. "The Antiociceptive Effects of Prostaglandin Antagonists in the Rat," *European Journal of Pharmacology*, 133, 249–256 (1987)–Europe.
F. R. George, et al. "Antagonism of Alcohol Hypnosis by Blockade of Prostaglandin Synthesis and Activity: Genotype and Time Course Effects," *Pharmacology, Biochemistry & Behavior*, vol. 19, 131–136 (1983)–USA.

(List continued on next page.)

*Primary Examiner*—Philip I. Datlow
*Attorney, Agent, or Firm*—Roberta L. Hastreiter; Roger A. Williams

[57] ABSTRACT

The present invention provides substituted dibenzoxazepine and dibenzthiazepine compounds of Formula I:

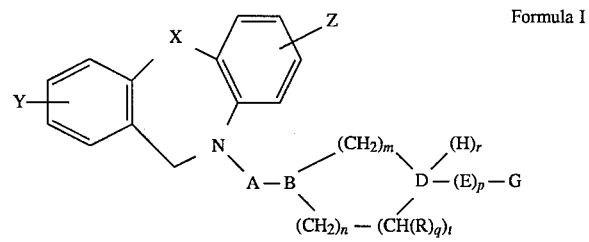

Formula I which are useful as analgesic agents for the treatment of pain, and for prostaglandin-$E_2$ mediated diseases, pharmaceutical compositions comprising a therapeutically-effective amount of a compound of Formula I in combination with a pharmaceutically-acceptable carrier, a method for eliminating or ameliorating pain in an animal comprising administering a therapeutically-effective amount of a compound of Formula I to the animal, and a method for treating prostaglandin-$E_2$ mediated diseases in an animal comprising administering a therapeutically-effective amount of a compound of Formula I to the animal.

11 Claims, No Drawings

OTHER PUBLICATIONS

R. Gimet, et al. "Quantitative Determination of Polymorphic Forms in a Formulation Matrix Using the Near Infra–Red Reflectance Analysis Technique," *Journal of Pharmaceutical & Biomedical Analysis*, vol. 5, No. 3, 205–211 (1987)–Great Britain.

A. Gomes, et al. "Pharmacodynamics of Venom of the Centipede *Scolopendra Subspinipes Dehaani*," *Indian Journal of Experimental Biology*, vol. 20, 615–618, Aug. (1982)–India.

K. Gyrires, et al. "The Use of the Writhing Test in Mice for Screening Different Types of Analgesics," *Arch. Int. Pharmacodyn*, 267, 131–140 (1984)–USA.

D. E. MacIntyre, et al. "Antagonism of Human Platelet Responses to Stimulatory and Inhibitory Prostaglandins," *Prog. Lipid. Res.*, 20 (1–4), 453–9 (1981)–USA.

C. A. Maggi, et al. "The Effect of SC–19220, a Prostaglandin Antagonist, on the Micturition Reflex in Rats," *European Journal of Pharmacology*, 152, 273–279 (1988)–Europe.

K. Nagarajan, et al. "Synthesis of 10,11–Dihydrodibenz[b,f][1,4]oxazepine Derivatives as Potential Anticonvulsant & Psychotropic Agents," *Indian Journal of Chemistry*, vol. 24B, 840–844 (1985)–India.

S. Nakajyo, et al. "Inhibitory Effect of Bassianolide, a Cyclodepsipeptide, on Drug–Induced Contractions of Isolated Smooth Muscle Preparations," *Japan J. Pharmacol.*, 32, 55–64 (1982)–Japan.

A. Rakovska, et al. "Antagonistic Effect of SC–19220 on the Responses of Guinea–Pig Gastric Muscles to Prostaglandins $E_1$, $E_2$, and $F_{2a}$", *Arch. Int. Pharmacodyn.*, 268, 59–69 (1984)–USA.

J. H. Sanner "Dibenzoxazepine Hydrazides as Prostaglandin Antagonists," *Intra–Science Chem. Rept.*, vol. 6, No. 1, 1–9 (1972)–USA.

J. H. Sanner, et al. "Structure–Activity Relationships of Some Dibenzoxazepine Derivatives as Prostaglandin Antagonists," *Advances in the Biosciences*, 9, 139–148 (1972)–USA.

M. E. Grieg, et al. "Effects of a Group of Dibenzoxazepines on Fatal Systemic Analphylaxis in Mice, Rats, and Guinea Pigs," *Journal of Medicinal Chemistry*, vol. 14, No. 2, 153–156 (1971)–USA.

U.S. Application 07/813,316 Hagen Dec. 20, 1991.
U.S. Application 08/021,694 Dapper Feb. 24, 1993.
U.S. Application 08/056,704 Chandrakumar Apr. 30, 1993.
U.S. Application 08/069,503 Chandrakumar May 28, 1993.
U.S. Application 08/134,345 Chandrakumar Oct. 7, 1993.
U.S. Application 08/133,681 Chandrakumar Oct. 7, 1993.

M. Protiva, et al. "Aminoalkyl Derivatives of Acridane and Phenthiazine Homologs of Pharmacodynamic Interest," *Experimentia*, vol. 13 (7), pp. 291–292 (1957).

J. Jilek, et al. "Neurotropic and Psychotropic Substances III. Derivatives of Dibenz [b,f][1,4]oxazepine," *Collection Czechoslov. Chem Commun.*, vol. 30, 463–471 (1965).

2-,3-,4-,5-,6-,7-,8-,9- AND/OR 10-SUBSTITUTED DIBENZOXAZEPINE AND DIBENZTHIAZEPINE COMPOUNDS, PHARMACEUTICAL COMPOSITIONS AND METHODS OF USE

This Application is a Continuation-In-Part Application of application U.S. Ser. No. 08/079,021, filed on Jun. 16, 1993, now U.S. Pat. No. 5,354,747.

BACKGROUND OF THE INVENTION

(1) Field of the Invention

The present invention generally relates to compounds having pharmacological activity which are useful as pharmaceutical agents and, more particularly, as analgesic agents for the treatment of pain, to pharmaceutical compositions containing one or more of these compounds, and to methods of treatment employing these compounds. More particularly, the present invention concerns substituted dibenzoxazepine compounds, pharmaceutical compositions containing one or more of these compounds in combination with a pharmaceutically-acceptable carrier, and medical methods of treating pain employing these compounds.

Analgesic compounds are agents which alleviate pain without causing a loss of consciousness and, thus, which are useful for treating pain and, often, for reducing inflammation.

The major classes of analgesic compounds include narcotic analgesics, or opiates, compounds which alleviate pain and induce sleep, and analgesic-antipyretic compounds, compounds which alleviate pain and reduce fever, such as salicylates.

Although the efficacy of opiates in relieving pain is well established, the associated addiction liability of opiates is a distinct disadvantage of these compounds.

While salicylate and salicylate-like agents (non-steroidal antiinflammatory agents or NSAIDS) are also efficacious in relieving pain, they often exhibit undesirable side effects, such as gastrointestinal irritation, as with aspirin, allergic response, as with aspirin, and/or liver toxicity with extended use, as with acetaminophen.

The compounds of the present invention are neither opiates nor salicylates, and represent another class of compounds which are useful as analgesic agents.

(2) Description of the Related Art

U.S. Pat. No. 3,357,998 discloses amides of dihydrodibenzo[b,f][1,4]oxazepine-10-carboxylic acids.

U.S. Pat. No. 3,644,346 discloses semicarbazones of dibenzoxazepine-N-carboxylic acid hydrazides.

U.S. Pat. No. 4,221,715 discloses dibenz[b,f][1,4]oxazepine-11-yl pyridinium salts and derivatives thereof.

U.S. Pat. No. 4,434,171 discloses 5,6-dihydro-5-(4-piperidinyl)-11H-dibenz[b,e]azepines.

U.S. Pat. No. 4,360,525 discloses 10-(4-piperidinyl)-10,11-dihydro-dibenz[b,f][1,4]oxazepines, -dibenzo[b,f][1,4]thiazepines and -5H-dibenzo[b,e][1,4]diazepines.

U. S. Pat. No. 4,379,150 discloses dibenz[b,f][1,4]-oxazepine derivatives which are substituted at the 10-position with the group —A—NR$_4$R$_5$, wherein A is a lower alkylene group, and wherein R$_4$ and R$_5$ may be taken together with a nitrogen atom to form a heterocyclic ring.

European Patent Application Publication Nos. 0 534 667 A1 and 0 480 641 A1 disclose tricyclic heterocycles which are stated to counteract mild to moderate pain by virtue of their anti-hyperalgesic properties.

German Patent Application Publication No. 1,170,322 discloses dibenz[b,f][1,4]oxazepine-11(10H)-ones which are substituted at the 10-position with the group —A—CO—NR$_5$R$_6$, wherein A may be a saturated aliphatic hydrocarbon group, and wherein R$_5$ and R$_6$ may represent cycloalkyl.

CH 648-309-A discloses N-methyl-piperidinyl dibenzazepine derivatives for use as neuroleptics, antidepressants and hypnotics.

K Nagarajan et al., "Synthesis of 10,11-Dihydrodibenz[b,f][1,4]oxazepine Derivatives as Potential Anticonvulsants & Psychotropic Agents,"*Indian Journal of Chemistry*, 24B, 840–844 (1985), disclose the synthesis of acyl, carbamoyl and thiocarbamoyl derivatives of 10,11-dihydrodibenz[b,f][1,4]oxazepine, most of which have either a nitro or an amino group at position-2, as analogues of carbamazepine, and the evaluation of these derivatives as anticonvulsants associated with neuroleptic activity.

W. E. Coyne et al , "Anticonvulsant Semicarbazides," *J. Med. Chem.*, 11(6), 1158–1160 (1968), disclose the investigation of the structure-activity relationship of the anticonvulsant activity of a series of semicarbazides which was synthesized from various tricyclic amines (see Table I, Page 1160).

Margaret E. Greig et al., "Effects of a Group of Dibenzodiazepines on Fatal Systemic Anaphylaxis in Mice, Rats and Guinea Pigs," *J. Med. Chem.*, 14(2), 153–153 (1970), discloses a series of dibenzodiazepines which was tested for protection against fatal systemic anaphalaxis in mice, rats and guinea pigs.

Each of the documents described hereinabove discloses compounds which are structurally different from the compounds of the present invention. Thus, the compounds of the present invention are structurally distinct from that which has been described in the art.

Compounds within the present invention have been found to exhibit activity as prostaglandin E$_2$ antagonists, and have been found to have few side effects, and no potential for the release of hydrazine, which is toxic.

SUMMARY OF THE INVENTION

The present invention provides compounds having a structure of Formula I:

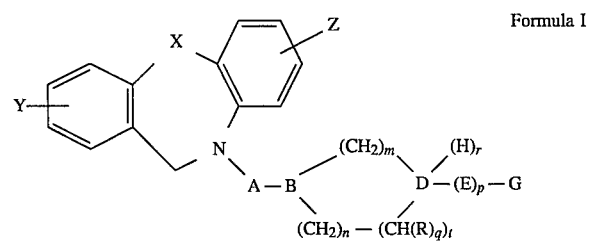

Formula I or a pharmaceutically-acceptable salt thereof, wherein:
X is oxygen, sulfur,

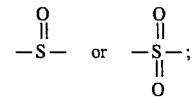

Y is hydrogen, halogen or hydroxy;

Z is hydrogen or halogen;

A is alkylene or carbonyl;

B is —CH or nitrogen;

D is carbon or nitrogen;

is alkylene, carbonyl, alkyleneamino or alkylenecarbonyl;

G is hydrogen, alkyl, cycloalkyl, alkoxy, aminoalkyl, aminocycloalkyl, aryl, alkylaryl or aryl-substituted aryl;

R is hydrogen or —$CO_2R^1$;

$R^1$ is hydrogen or alkyl;

m is an integer of from 0 to 4;

n is an integer of from 0 to 4;

r is 0 or 1;

q is an integer of from 0 to 1;

t is an integer of from 0 to 1; and p is an integer of from 0 to 1;

with the proviso that B and D cannot both be —CH, with the proviso that B cannot be —CH when p is 0 and G is alkyl, with the proviso that m and n are not each 0, with the proviso that G is not alkyl or cycloalkyl when X is sulfur, A is alkylene, B is —CH and D is nitrogen, with the proviso that G is not aminoalkyl or aminocycloalkyl when X is oxygen or sulfur, A is alkylene, B is nitrogen, R is hydrogen, D is carbon, r is 1 and p is 0.

The present invention also provides pharmaceutical compositions which are pharmaceutically acceptable and which comprise a therapeutically-effective amount of a compound of Formula I in combination with a pharmaceutically-acceptable carrier, and a method for eliminating or ameliorating pain in an animal comprising administering a therapeutically-effective amount of a compound of Formula I to the animal.

DETAILED DESCRIPTION OF THE INVENTION

Definitions

For purposes of clarity, the terms and phrases used throughout this specification and the appended claims are defined in the manner set forth directly below.

Some of the chemical structures which are presented in this specification and the appended claims have been drawn using the convention which employs lines to represent alkyl radicals, which is known by those of skill in the art.

The abbreviations "AcOH" and "HOAc" as used herein mean acetic acid.

The term "alkyl" as used herein means a saturated hydrocarbon radical having from one to ten carbon atoms, and within which includes from one to six carbon atoms, and further within which includes from one to three carbon atoms, which can be a straight or branched chain. Representative of such radicals are methyl, ethyl, propyl, isopropyl, butyl, sec-butyl, isobutyl, tert-butyl, pentyl and the like.

The term "alkylene" as used herein means a straight or branched saturated hydrocarbon chain spacer arm which has from one to ten carbon atoms, and within which includes from one to six carbon atoms, and further within which includes one, two or three carbon atoms.

The term "alkyleneamino" as used herein means an alkylene group, as defined above, having an —NH— group attached thereto.

The term "alkylenecarbonyl" as used herein means an alkylene group, as defined above, having a carbonyl group attached thereto, as defined below.

The term "alkylaryl" as used herein means an alkyl group, as defined above, having an aryl group, as defined below, attached thereto.

The term "alkoxy" as used herein means an alkyl group, as defined above, having an oxygen atom attached thereto. Representative alkoxy groups include methoxy, ethoxy, propoxy, tert-butoxy and the like.

The abbreviation "$AlMe_3$" as used herein means trimethylaluminum.

The term "amino" as used herein means an —$NH_2$ group.

The term "aminoalkyl" as used herein means an amino group, as defined above, having one or two alkyl groups attached thereto. Representative aminoalkyl groups include aminomethyl, aminoethyl, aminopropyl, aminobutyl, aminopentyl and the like.

The term "aminocycloalkyl" as used herein means a cycloalkyl group, as defined below, which has a nitrogen atom, attached thereto.

The term "analgesia" as used herein means the reduction, or absence, of sensibility to pain, designating particularly the relief of pain without loss of consciousness.

The term "animal" as used herein includes mammals and nonmammals, and further includes humans and non-human mammals.

The term "aryl" as used herein means 5- and 6-membered single-ring aromatic radicals, and 10-membered double-ring aromatic radicals, which may include from zero to four heteroatoms, and within which includes from zero to three heteroatoms, and within which further includes from zero to two heteroatoms, and within which further includes from zero to one heteroatom. Representative aryls include phenyl, thienyl, furanyl, pyridinyl, imidazolyl, thiazolyl, pyrimidinyl, pyrazinyl, pyridazinyl, (is)oxazolyl, triazolyl, tetrazolyl, pyrrolyl, pyridinyl-N-oxide and the like.

The phrase "aryl-substituted aryl" as used herein means an aryl group, as defined above, which has an aryl group, as defined above, or an alkylaryl group, as defined above, attached thereto.

The abbreviation "Boc" as used herein means t-butyloxycarbonyl.

The abbreviation "Calc." as used herein means calculated.

The term "carbonyl" as used herein means a

group.

The term "carboxy" as used herein means a

group.

The term "composition" as used herein means a product which results from the combining of more than one element or ingredient.

The term "cyano" as used herein means a —CN group.

The term "cycloalkyl" as used herein means a nonaromatic cyclic ring radical having from one to ten carbon atoms, and within which includes from one to six carbon atoms, and further within which includes from one to three carbon atoms, such as cyclohexane.

The abbreviation "DMAP" as used herein means 4-(dimethylamino)pyridine.

The abbreviation "DMF" as used herein means dimethylformamide.

The abbreviation "DR" as used herein means dose ratio.

The abbreviation "DSC" as used herein means Differential Scanning Calorimetry.

The phrase "$EC_{50}$ concentration" as used herein means that concentration of a compound or drug which is necessary to elicit a 50% maximal biological response and, thus, which is necessary to elicit a 50% reduction in the contractions of guinea pig ileum segments in a prostaglandin antagonism assay.

The phrase "$ED_{50}$ dose" as used herein means that dose of a compound or drug which produced a biological effect, such as producing analgesia, in 50% of the animals to which the compound or drug was administered.

The abbreviation "Et" as used herein means ethyl (—$CH_2CH_3$).

The abbreviation "$Et_2$" as used herein means ether.

The abbreviation "$Et_2O$" as used herein means diethyl ether.

The abbreviation "EtOAc" as used herein means ethyl acetate.

The abbreviation "EtOH" as used herein means ethanol ($CH_3CH_2OH$).

The abbreviation "$Et_3N$" as used herein means triethylamine.

The term "halo" or "halogen" as used herein means chlorine (Cl), bromine (Br), fluorine (F) and/or iodine (I).

The term "heteroatom" as used herein means an atom of any element other than carbon or hydrogen.

The abbreviation "$^1H$ NMR" as used herein means Proton Nuclear Magnetic Resonance.

The abbreviation "HPLC" as used herein means High Pressure Liquid Chromatography.

The term "hydroxy" as used herein means the group —OH.

The term "intragastrically" and/or the abbreviation "i.g." as used herein means that a compound or drug was administered into the stomach.

The abbreviation "i.p." as used herein means that a compound or drug was administered intraperitoneally.

The abbreviation "IR" as used herein means infrared, referring to an infrared spectrum.

The abbreviation "LAH" as used herein means lithium aluminum hydride.

The abbreviation "Me" as used herein means methyl (—$CH_3$).

The abbreviation "MeOH" as used herein means methanol ($CH_3OH$).

The abbreviation "mp" as used herein means melting point.

The abbreviation "MPLC" as used herein means Medium Pressure Liquid Chromatography.

The term "nitro" as used herein means an —$NO_2$ group.

The abbreviation "n-BuLi" as used herein means n-butyl lithium.

The abbreviation "NMR" as used herein means Nuclear Magnetic Resonance.

The abbreviation "n-Pr" as used herein means n-propyl.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, as defined directly above, such as a liquid or solid filler, diluent, excipient, solvent or encapsulating material, involved in carrying or transporting a chemical compound or pharmaceutical agent from one organ, or portion of the body, to another organ, or portion of the body. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The phrase "pharmaceutically-acceptable salts" as used herein refers to non-toxic salts of the compounds of the present invention which are generally prepared by reacting the free base with a suitable organic or inorganic acid, or which are prepared by reacting the free acid with a suitable base. Representative salts include the hydrochloride, hydrobromide, sulfate, bisulfate, acetate, valerate, oleate, palmitate, stearate, laurate, benzoate, lactate, phosphate, tosylate, citrate, maleate, fumarate, succinate, tartrate, napsylate, clavulanate and the like salts, and alkali metal salts, such as sodium and potassium, and alkaline earth salts, such as calcium and magnesium.

The abbreviation "p.o." as used herein means that a compound or drug was administered orally.

The phrase "protecting group" as used herein means substituents which protect the reactive functional group from undesirable chemical reactions. Examples of such protecting groups include esters of carboxylic acids, ethers of alcohols and acetals and ketals of aldehydes and ketones.

The phrase "N-protecting group" or "N-protected" as used herein means those groups intended to protect the N-terminus of an amino acid or peptide, to protect an amino group against undesirable reactions during synthetic procedures and includes, but is not limited to, sulfonyl, acetyl, pivaloyl, t-butyloxycarbonyl (Boc), carbonylbenzyloxy (Cbz), benzoyl and an L- or D-aminoacyl residue, which may itself be N-protected similarly.

The abbreviation "RaNi" as used herein means Raney nickel.

The abbreviation "s.c." as used herein means that a compound or drug was administered subcutaneously.

The term "sulfonyl" as used herein means an

group.

The abbreviation "t-Bu" as used herein means tert-butyl.

The abbreviation "TEA" as used herein means triethylamine.

The phrase "therapeutically-effective amount" as used herein means an amount of a compound, material, or composition which is an effective dose for eliminating or ameliorating pain in an animal, or for producing some other desired therapeutic effect, at a reasonable benefit/risk ratio applicable to any medical treatment.

The abbreviation "THF" as used herein means tetrahydrofuran.

The phrases "title compound," "title product" and "title material" as used herein mean that compound, product or material whose chemical name is given, and/or whose structure is shown, in the particular example, or subpart thereof, referred to. If no particular example, or subpart thereof, is referred to, it means that compound, product or material whose chemical name is given, and/or whose structure is shown, in the particular example, or subpart thereof, in which it appears.

Description of Invention

In one aspect, the present invention provides compounds comprising a structure of Formula I, as described above, and pharmaceutically-acceptable salts, esters and amides thereof.

The compounds of the present invention comprise a class of substituted dibenzoxazepine and dibenzthiazepine compounds in which the 2-, 3-, 4-, 5-, 6-, 7-, 8-, 9- and/or 10-position is substituted. Compounds within the present invention have been shown to exhibit activity as prostaglandin $E_2$ antagonists.

Specific compounds within the scope of the invention include, but are not limited to, the compounds discussed in the examples presented below, as well as their pharmaceutically-acceptable salts, esters, and amides.

Contemplated equivalents of the compounds described in Formula I include compounds which otherwise correspond thereto, and which have the same general properties thereof, wherein one or more simple variations of substituents are made which do not adversely affect the efficacy of the compound.

Certain compounds of this invention may exist in geometric or stereoisomeric forms. The present invention contemplates all such compounds, including cis- and trans-geometric isomers, R- and S-enantiomers, diastereomers, d-isomers, l-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Certain compounds of the present invention may contain a basic functional group, such as amino, alkylamino or dialkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, S. M. Berge et al., "Pharmaceutical Salts," *J. Pharm. Sci.*, 66 1–19 (977), which, as well as all other documents referred to herein, is incorporated herein by reference.)

In other cases, the compounds of the invention may contain one or more acidic functional groups, such as carboxyl and the like, and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, S. M. Berge et al., "Pharmaceutical Salts," supra.)

In another aspect, the present invention provides pharmaceutically-acceptable compositions which comprise a therapeutically-effective amount of one or more of the compounds of Formula I, as described hereinabove, formulated together with one or more pharmaceutically-acceptable carriers. The pharmaceutical compositions of the invention may be specially formulated for oral administration in solid or liquid form, for parenteral injection, or for rectal or vaginal administration.

In yet a further aspect, the present invention provides a method for eliminating or ameliorating pain in an animal, or for producing some other therapeutic effect in an animal, such as for treating Prostaglandin-$E_2$ mediated diseases, as discussed in more detail hereinbelow, comprising administering a therapeutically-effective amount of a compound of Formula I, as described hereinabove, to the animal.

The preferred embodiments of this invention are the compounds described in Examples 24, 34 and 58 below. The most preferred embodiment of the invention is the compound described in Example 24 below.

Utility

Compounds within the present invention, and the pharmaceutical compositions comprising one or more of these compounds, are useful as analgesic agents for the elimination or amelioration of pain in animals.

Compounds of the present invention exhibit activity as prostaglandin $E_2$ antagonists (prostaglandin antagonists of the $E_2$ series). Thus, they would be useful for the treatment of diseases in an animal which are responsive to prostaglandin-$E_2$ antagonists.

In addition to treating pain, the compounds and compositions of the present invention would be useful in treating convulsions, ischemia and other central nervous system disorders, as well as osteoporosis, dysmenorrhea, asthma, enuresis, arrhythmia, urinary incontinence, gastric hypermotility, irritable bowel syndrome and diarrhea, by virtue of their activity as prostaglandin $E_2$ antagonists.

Methods of Preparation

In general, the compounds of the present invention may be prepared by the methods illustrated in the following general reaction schemes, or by modifications thereof, using readily available starting materials, reagents and conventional synthesis procedures. Unless otherwise specified, the various substituents of the compounds are defined in the same manner as they are defined above in Formula I in the "Summary of Invention" section.

If a particular enantiomer of a compound of the present invention is desired, it may be prepared by chiral synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

In General Reaction Scheme No. 1, the sodium salt of a substituted or unsubstituted (Y is hydrogen, halogen or hydroxy) 2-hydroxy or 2-thiol benzaldehyde is generated by treatment with sodium hydride (NaH) in dimethylformamide (DMF). This material is heated with a substituted or unsubstituted (Z is hydrogen or halogen) 2-dichloro nitrobenzene. The nitro group of the condensate is reduced to an amino function with hydrogen using raney nickel as catalyst. Spontaneous cyclization of the amino group with the aldehyde occurs with a subsequent dehydration and further reduction to the dibenzoxazepine or dibenzthiazepine product. By treatment of this product with phosgene in toluene, the carbamoyl chloride (A equals carbonyl) is produced. This material is condensed with a cyclic secondary amine (B is nitrogen) in methylene chloride solution. The reaction is carried out in the presence of an equivalent of triethyl amine to neutralize the HCl generated in the transformation and molecular sieves to remove any water in the system.

The cyclic secondary amine is a compound in which, when D is —CH, m and n may be the same or different, and may each be an integer independently of from 0 to 4, but not each being zero, and t is an integer of from 0 to 1. When t is 1, q is 1, R is hydrogen or —$CO_2R^1$ and $R^1$ is either hydrogen or alkyl. In either case, where t is 0 or 1, E is alkylene, carbonyl, alkyleneamino, or alkylenecarbonyl, p is an integer from 0 to 1, and G is hydrogen, alkyl, cycloalkyl, alkoxy, aminoalkyl, aminocycloalkyl, aryl, alkylaryl or aryl-substituted aryl.

The cyclic secondary amine is also a compound in which, when D is carbon, m or n may be the same or different, and may each be an integer independently of from 0 to 4, but not each being zero. In this case, t is only 1, q is then 0, E is alkylene, carbonyl, alkyleneamino, or alkylenecarbonyl, p is an integer of from 0 to 1, and G is hydrogen, alkyl, cycloalkyl, alkoxy, aminoalkyl, aminocycloalkyl, aryl, alkylaryl or aryl-substituted aryl.

The cyclic secondary amine is also a compound in which, when D is nitrogen, m may be an integer of from 2 to 4 and n may be an integer of from 1 to 4. In this case, t is 0 or 1 and, when t is 1, q is 1 and R is hydrogen or —$CO_2R^1$ The group $R^1$ is either hydrogen or alkyl and E is alkylene, carbonyl, alkyleneamino or alkylenecarbonyl, p is an integer of from 0 to 1 and G is hydrogen, alkyl, cycloalkyl, alkoxy, aminoalkyl, aminocycloalkyl, aryl, alkylaryl or aryl-substituted aryl.

If a basic atom is present in the molecule, the HCl salt is generated by treatment of the product amine in diethyl ether or methanol with 6N HCl/dioxane. Either the free bases or HCl salts, in the case where X is sulfur, may be oxidized to the sulfoxide by treatment with 30% $H_2O_2$ in acetic acid at room temperature, and to the sulfone by treatment with 30% $H_2O_2$ in acetic acid at 50° C.

In General Reaction Scheme No. 2, an alternative and complementary procedure is used for obtaining compounds of this invention. Thus, in this scheme, the carbamoyl chloride (A equals CO—Cl) of either tricycle as defined in the discussion for General Reaction Scheme No. 1 is condensed with cyclic secondary amines where B and D are both nitrogen, m may be an integer of from 2 to 4 and n may be an integer of from 1 to 4. In this case, t is 0 or 1 and, when t is 1, q is 1 and R is hydrogen or —$CO_2R^1$. The group $R^1$ is alkyl, E is a carbonyl, p is 1 and G is alkoxy. The reaction is carried out in the presence of an equivalent of triethyl amine to neutralize the HCl generated in the transformation and molecular sieves to remove any water in the system. The alkoxy carbonyl function is then removed either by treatment with HCl in dioxane or with sodium hydroxide and hydrazine in dioxane. The product of this reaction is then coupled to an acid function represented by HO—E—G where E is a carbonyl, p is 1 and G is alkyl, cycloalkyl, aryl, alkylaryl or aryl-substituted aryl. The coupling is achieved by reacting the above reagents with 1-(3-dimethylaminopropyl)-3-ethylcarbodiimide hydrochloride, 1-hydroxy benzotriazole hydrate, and triethyl amine in dimethylformamide (DMF) solution.

If a basic nitrogen is present in the molecule, the HCl salt is generated by treatment of the product amine in diethyl ether with 6N HCl/dioxane. Either the free bases or HCl salts, in the case where X is sulfur, may be oxidized to the sulfoxide by treatment with 30% $H_2O_2$ in acetic acid at room temperature and to the sulfone by treatment with 30% $H_2O_2$ in acetic acid at 50° C.

In General Reaction Scheme No. 3, an alternative and complementary procedure is used for obtaining compounds of this invention. Thus, in this scheme, the cyclic secondary diamine (B and D are each nitrogen) is a compound where one of the amines is protected with a tert-butoxy carbonyl function (Boc), n and m are each integers of from 2 to 4, and t is 0. This material is coupled to an acid where E is a carbonyl, p is 1, and G is alkyl, cycloalkyl, aryl, alkylaryl or aryl-substituted aryl. The coupling is achieved by reacting the above reagents with 1-(3-dimethylaminopropyl)-3-ethylcarbodiimide hydrochloride, 1-hydroxy benzotriazole hydrate, and triethyl amine, in DMF solution or with isobutylchloroformate and N-methylmorpholine in methylene chloride solution. The cyclic secondary diamine is also coupled to an aldehyde where E is a carbonyl and G is alkyl, cycloalkyl, aryl, alkylaryl or aryl-substituted aryl. This reaction is carried out in the presence of sodium cyanoborohydride in methanol or hydrogen in methanol using Pd/C as catalyst.

The Boc protecting group is removed from these products by treatment with 6N HCl/dioxane in acetic acid. The resulting HCl salt is then condensed with the carbamoyl chloride (A equals CO—Cl) of either tricycle as defined in the discussion for General Reaction Scheme No. 1. The reaction is carried out in methylene chloride in the presence of two equivalents of triethyl amine to neutralize the HCl of the amine reactant and the HCl generated in the transformation and molecular sieves to remove any water in the system.

If a basic nitrogen is present in the molecule, the HCl salt is generated by treatment of the product amine in either diethyl ether or methanol with 6N HCl/dioxane. Either the free bases or HCl salts, in the case where X is sulfur, may be oxidized to the sulfoxide by treatment with 30% $H_2O_2$ in acetic acid at room temperature, and to the sulfone by treatment with 30% $H_2O_2$ in acetic acid at 50° C.

In General Reaction Scheme No. 4, another alternative and complementary procedure is used for obtaining compounds of this invention. Thus, in this scheme, either tricycle, as defined in the discussion of General Reaction Scheme No. 1, is reacted with a cyclic compound containing a displaceable function J which is halogen or alkyl or aryl sulfonate. This cyclic compound is a material where D is carbon or nitrogen, m and n may be the same or different, and may each be an integer of from 0 to 4, but not each being zero. In this case, t is 0, E is alkylene, carbonyl, alkyleneamino or alkylenecarbonyl, p is an integer of from 0 to 1, and G is hydrogen, alkyl, cycloalkyl, alkoxy, aminoalkyl, aminocycloalkyl, aryl, alkylaryl or aryl-substituted aryl.

If a basic nitrogen is present in the molecule, the HCl salt is generated by treatment of the product amine in either diethyl ether or methanol/water with 6N HCl/dioxane. Either the free bases or HCl salts, in the case where X is sulfur, may be oxidized to the sulfoxide by treatment with 30% $H_2O_2$ in acetic acid at room temperature, and to the sulfone by treatment with 30% $H_2O_2$ in acetic acid at 50° C.

GENERAL REACTION SCHEME NO. 1

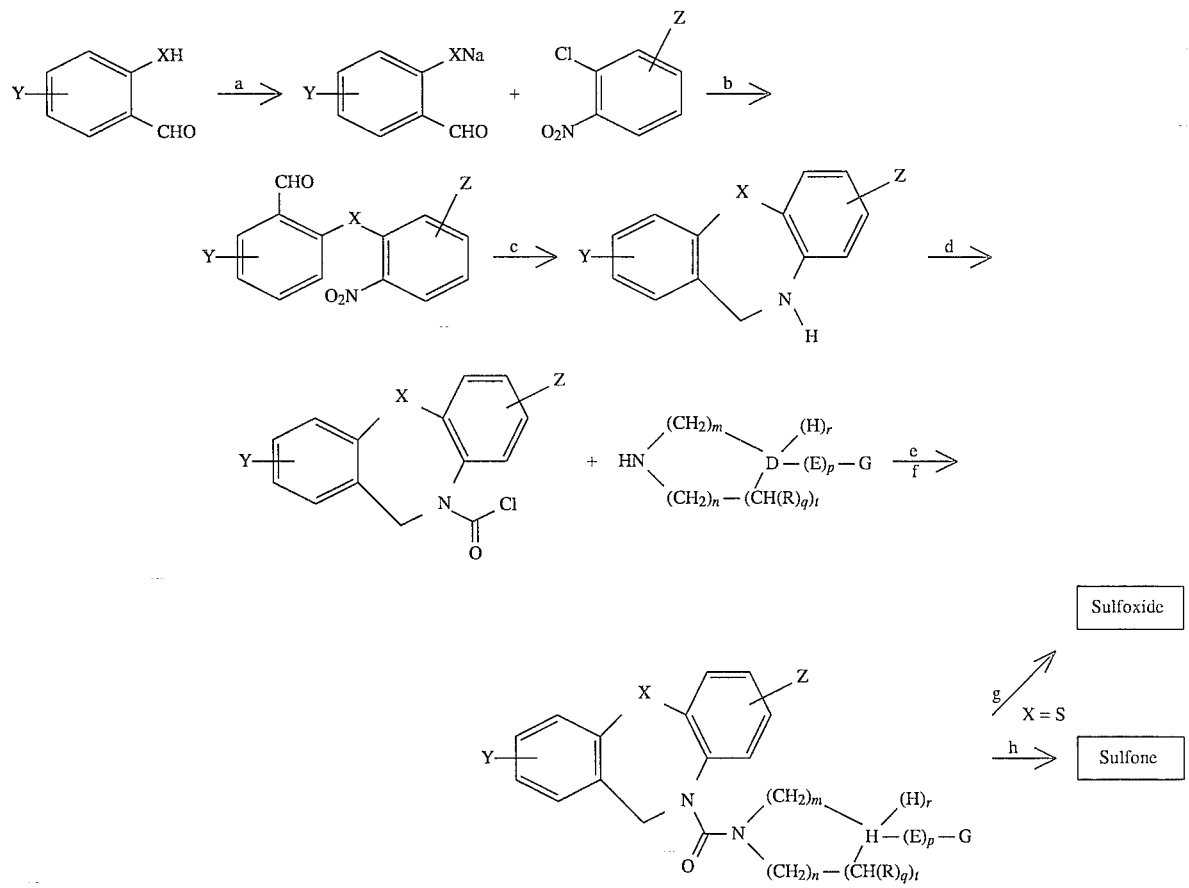

-continued
GENERAL REACTION SCHEME NO. 1

(a) sodium hydride, dimethylformamide.
(b) heat.
(c) hydrogen, raney nickel catalyst.
(d) phosgene in toluene.
(e) triethyl amine, methylene chloride, molecular sieves.
(f) 6N HCl/dioxane, diethyl ether or methanol and water.
(g) where X = S; 30% $H_2O_2$, acetic acid, room temperature.
(h) where X = S; 30% $H_2O_2$, acetic acid, 50° C.

GENERAL REACTION SCHEME NO. 2

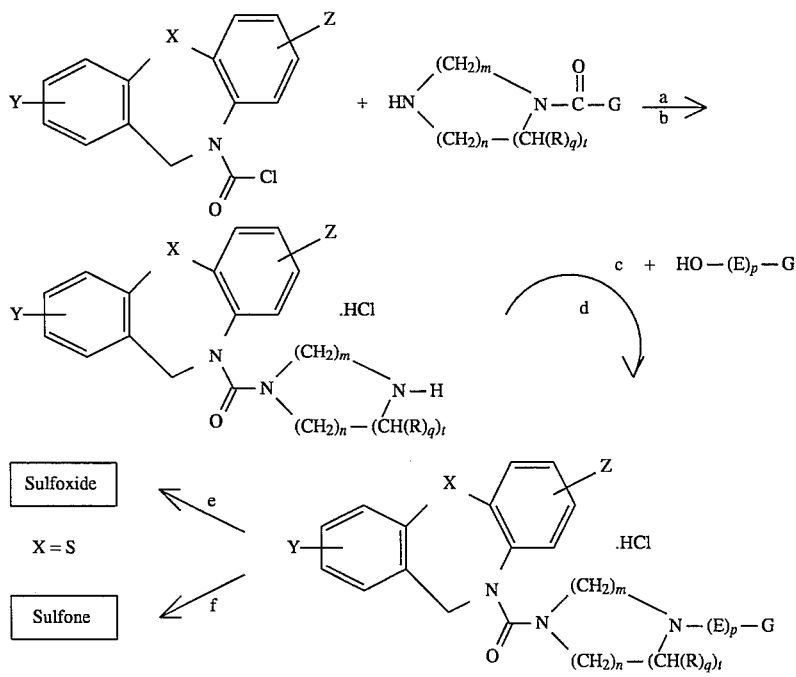

(a) triethyl amine, methylene chloride, molecular sieves.
(b) 6N HCl/dioxane, acetic acid or concentrated HCl, dioxane or NaOH, hydrazine, dioxane.
(c) 1-(3-dimethylaminopropyl)-3-ethylcarbodiimide hydrochloride, 1-hydroxy benzotriazole hydrate, triethyl amine, dimethylformamide.
(d) 6N HCl/dioxane, diethyl ether, when a basic, HCl salt forming group is present.
(e) where X = S; 30% $H_2O_2$, acetic acid, room temperature.
(f) where X = S; 30% $H_2O_2$, acetic acid, 50° C.

GENERAL REACTION SCHEME NO. 3

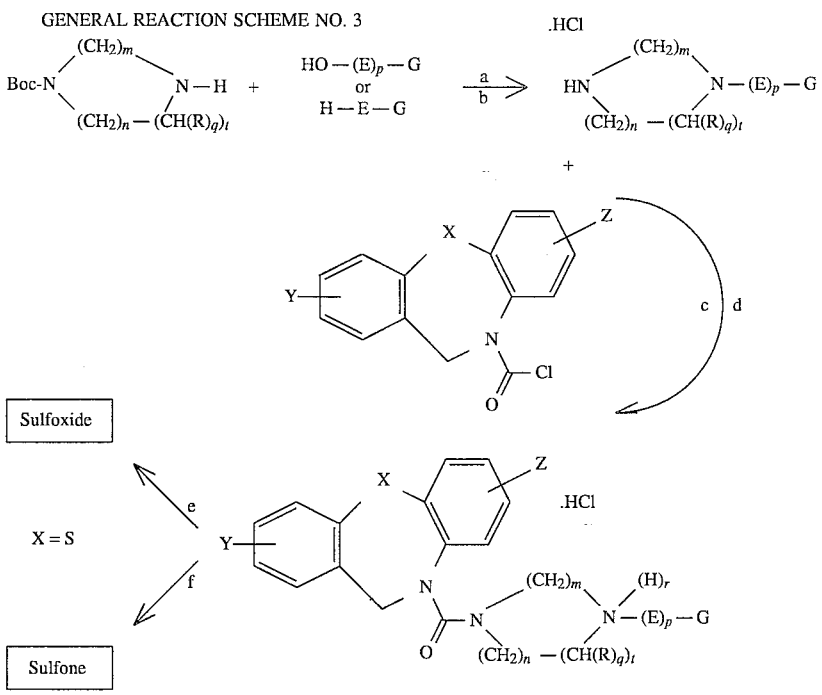

(a) For HO — E — G: isobutylchloroformate, N-methylmorpholine, methylene chloride, or 1-(3-Dimethylaminopropyl)-3-ethylcarbodiimide hydrochloride, 1-hydroxy benzotriazole hydrate, triethyl amine, dimethylformamide.
For H — E — G: sodium cyanoborohydride, methanol or hydrogen, Pd/C, methanol.
(b) 6N HCl/dioxane, acetic acid.
(c) triethyl amine, methylene chloride, molecular sieves.
(d) 6N HCl/dioxane, diethyl ether or methanol.
(e) where X = S; 30% $H_2O_2$, acetic acid, room temperature.
(f) where X = S; 30% $H_2O_2$, acetic acid, 50° C.

GENERAL REACTION SCHEME NO. 4

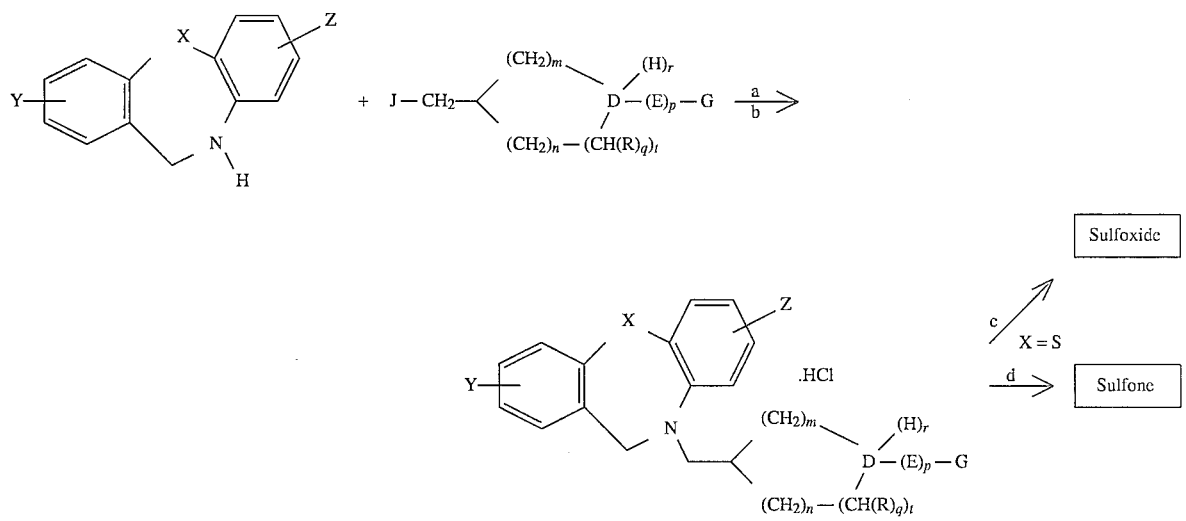

-continued
GENERAL REACTION SCHEME NO. 4

(a) diisopropylethyl amine, toluene, heat.
(b) 6N HCl/dioxane, diethyl ether or methanol and water.
(c) where X = S; 30% $H_2O_2$, acetic acid, room temperature.
(d) where X = S; 30% $H_2O_2$, acetic acid, 50° C.

The conditions for carrying out the individual steps in each of the general reaction schemes presented above are conventional, well-known, and capable of wide variation.

Other methods known in the art can also be used to synthesize the compounds of the present invention.

Dosage and Mode of Administration

The compounds of the present invention, and the pharmaceutical compositions comprising one or more of these compounds in combination with a pharmaceutically-acceptable carrier, are useful in treating pain in animals. A physician or veterinarian of ordinary skill in the art can readily determine whether or not a patient is in pain.

The pharmaceutical compositions of the present invention, which will typically comprise one or more of the compounds of Formula I as an active ingredient in admixture with one or more pharmaceutically-acceptable carriers and, optionally, with one or more other compounds, drugs or materials, are employed therapeutically and, thus, would generally be used under the guidance of a physician. The appropriate dosage and form of administration of these compositions will be suitably selected by methods which are consistent with conventional pharmaceutical practices.

The pharmaceutical compositions of the present invention may be specially formulated for oral administration in solid or liquid form, for parenteral injection, and/or for rectal or vaginal administration. They may be administered to humans and other animals for therapy by any suitable route of administration, including orally, nasally, as by, for example, a spray, rectally, intravaginally, parenterally, intracisternally and topically, as by powders, ointments or drops, including buccally and sublingually. While the preferred routes of administration are orally and parenterally, the most preferred mode of administration is orally.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the severity of the pain, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required to alleviate or ameliorate a particular patient's pain. For example, the physician or veterinarian could start doses of the compound of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, dosage levels in the range of from about 0.001 mg to about 10 g, more preferably from about 1 mg to about 1000 mg, of active compound per kilogram of body weight per day are administered to a mammalian patient. However, the total daily usage of the compounds of Formula I, or the pharmaceutical compositions comprising such compounds, will be determined by an attending physician or veterinarian within the scope of sound medical judgement.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

The pharmaceutical compositions of the present invention comprise a compound of the present invention together with one or more pharmaceutically-acceptable carriers thereof and, optionally, with other therapeutic agents. Each carrier must be "acceptable" in the sense of being compatible with the other ingredients of the formulation and not injurious to the patient.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfite, sodium metabisulfite, sodium sulfite and the like; (2) oil-soluble antioxidants, such as ascorbyl palmitate, butylated hydroxyanisole (BHA), butylated hydroxytoluene (BHT), propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient (compound of Formula I) which can be combined with a carrier material to produce a single dosage form will vary depending upon the host being treated, the particular mode of administration and all of the other factors described above. The amount of active ingredient which can be combined with a carrier material to produce a single dosage form will generally be that amount of the compound which is the lowest dose effective to produce a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, with one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient (compound of Formula I) is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient (compound of Formula I as described above), the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a Pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a Parenterally-administered drug form is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The injectable materials can be sterilized, for example, by filtration through a bacterial-retaining filter, or by incorporating sterilizing agents in the form of sterile solid compositions which can be dissolved or dispersed in sterile water or in other sterile injectable mediums just prior to use.

The formulations may be presented in unit-dose or multi-dose sealed containers, for example, ampoules and vials, and may be stored in a lyophilized condition requiring only the addition of the sterile liquid carrier, for example water for injections, immediately prior to use. Extemporaneous injection solutions and suspensions may be prepared from sterile powders, granules and tablets of the type described above.

The pharmaceutical compositions of the present invention may also be used in the form of veterinary formulations, including those adapted for the following: (1) oral administration, for example, drenches (aqueous or non-aqueous solutions or suspensions), tablets, boluses, powders, granules or pellets for admixture with feed stuffs, pastes for application to the tongue; (2) parenteral administration, for example, by subcutaneous, intramuscular or intravenous injection as, for example, a sterile solution or suspension or, when appropriate, by intramammary injection where a suspension or solution is introduced into the udder of the animal via its teat; (3) topical application, for example, as a cream, ointment or spray applied to the skin; or (4) intravaginally, for example, as a pessary, cream or foam.

While the various aspects of the present invention are described herein with some particularity, those of skill in the art will recognize numerous modifications and variations which remain within the spirit of the invention. These modifications and variations are within the scope of the invention as described and claimed herein.

EXAMPLES

The following examples describe and illustrate the methods for the preparation of the compounds of the present invention, as well as other aspects of the present invention, and the results achieved thereby, in further detail. Both an explanation of, and the actual procedures for, the various aspects of the present invention are described where appropriate. These examples are intended to be merely illustrative of the present invention, and not limiting thereof in either scope or spirit. Those of skill in the art will readily understand that known variations of the conditions and processes of the preparative procedures described in these examples can be used to prepare the compounds of the present invention, and the pharmaceutical compositions comprising such compounds.

In the examples, all parts are by weight unless otherwise indicated.

All equipment employed in the examples is commercially available. Unless otherwise indicated, all starting materials employed in the examples are commercially available. Sources for these materials include Sigma Chemical Co. (St. Louis, Mo.), Aldrich Chemical Co. (Milwaukee, Wis.), Lancaster Synthesis (Windham, N.H.), Fisher Scientific (Pittsburgh, Pa.), Boehringer Mannheim Biochemicals (Indianapolis, Ind.), Fluka Chemical Corp. (Ronkonkoma, N.Y.), Johnson Matthey Co. (West Deptford, N.J.), Eastman Kodak Co. (Rochester, N.Y.), Emkay Chemical Co. (Elizabeth, N.J.), Maybridge Chemical (Columbia, S.C.) and Chemical Dynamics Corp. (South Plainfield, N.J.). Most of the starting materials were obtained from Aldrich Chemical Co. (Milwaukee, Wis.).

All patents and publications referred to in the examples, and throughout the specification, are hereby incorporated herein by reference, without admission that such is prior art.

Example 1

8-chloro-10,11-dihydrodibenz[b,f][1,4]oxazepine

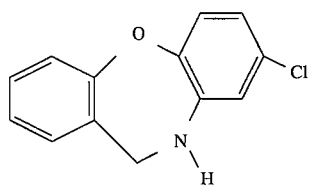

The synthesis of the title compound is described in U.S. Pat. No. 3,534,019, which is incorporated herein by reference.

Briefly, 200 parts of 2,5-dichloro-nitrobenzene were heated to 160° C. and stirred, and 160 parts of the potassium salt of salicylaldehyde was added over a period of 30 minutes. After the addition was complete, an exothermic reaction took place, and the temperature rose to about 195° C. Heating was discontinued until the reaction subsided, and the mixture was heated for 1 hour at 150° C. The mixture was cooled, ice and water were added, and it was extracted with ether ($Et_2O$). The ether layer was filtered to remove insoluble material, and the resultant solution was dried over sodium sulfate. The ether solvent was evaporated, and the residual oil was recrystallized from a mixture of hexane and benzene to give 2-(2-nitro-4-chlorophenoxy)benzaldehyde melting at about 100°–101° C.

A solution of 55 parts of the ether obtained in the preceding paragraph in 800 parts of ethanol was hydrogenated over Raney nickel catalyst at room temperature and atmospheric pressure. When hydrogen uptake ceased, the catalyst was removed by filtration, and the ethanol solvent was evaporated. The residue was dissolved in 500 parts by volume of hexane, filtered, and cooled. There was obtained yellowish-white crystals which were separated by filtration to give the title compound melting at about 94°–95° C.

Example 2

8-chlorodibenz[b,f][1,4]-oxazepine-10(11H)-carbonyl chloride (2)

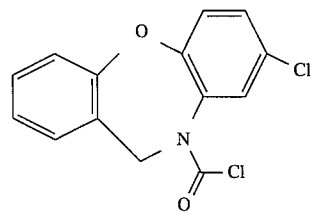

The title compound was also synthesized in the manner described in U.S. Pat. No. 3,534,019.

13 parts of phosgene in 45 parts of toluene was stirred for 2 hours at 5°–10° C., and then 70 parts of ether was added. This was followed by the addition of a solution of 18.9 parts of the title compound of Example 1 and 7.2 parts of triethylamine in 140 parts of ether. After the addition was complete, the mixture was stirred for 2 hours, and then was filtered. The solvent was then evaporated from the filtrate. The resulting residue was then dissolved in 200 parts by volume of hot hexane, and this mixture was then filtered and cooled.

Example 3

1-[{8-chlorodibenz[b,f][1,4]oxazepin-10(11H)-yl)carbonyl]-N,N-bis(2-hydroxyethyl)-4-piperidinecarboxamide

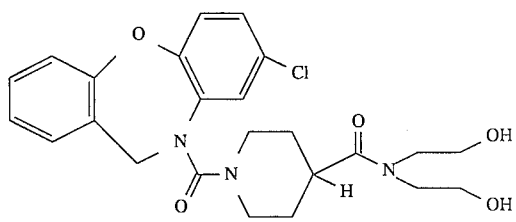

A sample of methyl isonicotinate (137 g, 1.0 mole) was heated neat with diethanolamine (126 g, 1 mole). After cooling to room temperature, the crystallized product was filtered, washed with isopropanol, washed with $Et_2O$, and dried in vacuo to yield 179 g (84%) of the desired diethanol isonicotinamide.

A 45.0 g sample (0.22 mole) of the diethanol isonicotinamide dissolved in 500 mL of dioxane was placed in a 2 L Parr bomb along with 4.5 g of $RuO_2$. The bomb was heated to 100° C. and maintained at this temperature for 30 minutes under a hydrogen pressure of 1000 psi. The bomb was cooled to room temperature and another 500 mL of dioxane were added. The reduction was run again at 100° C. for 30 minutes under a hydrogen pressure of 1000 psi. After cooling the reaction to room temperature and removal of the catalyst by filtration, the dioxane was decanted from the light tan product oil, N,N-bis(2-hydroxyethyl)-4-piperidinecarboxamide (36.7 g).

The title compound of Example 2 (1.0 g, 3.4 mmol) was combined with N,N-bis(2-hydroxyethyl)-4-piperidinecarboxamide (0.83 g, 4.1 mmol), triethylamine (0.41 g, 4.1 mmol), molecular sieves #3A (5 g), 60 mL of methylene chloride ($CH_2Cl_2$), and 8 mL dimethylformamide (DMF). After stirring this mixture for 24 hours at room temperature (rt) and under a nitrogen ($N_2$) atmosphere, it was filtered and the solid was washed liberally with ethyl acetate (EtOAc) and 0.5N potassium bisulfate ($KHSO_4$). The organic layer was separated from the filtrate, washed with 0.5N $KHSO_4$ and brine. After removing all solvent under reduced pressure, the residue oil (1.5 g) was chromatographed to yield 0.5 g of the title material.

Calculated for $C_{24}H_{28}N_3O_5Cl+0.25\ H_2O+0.1\ CH_2Cl_2$ (MW=486.95): C, 59.44; H, 5.94; N, 8.63; Cl, 8.74. Found: C, 59.78; H, 5.92; N, 8.49; Cl, 8.68.

Example 4

8-chloro-10,11-dihydro-10-[(octahydro-2H-pyrido[1,2-a]pyrazin-2-yl)carbonyl]dibenz[b,f][1,4]oxazepine

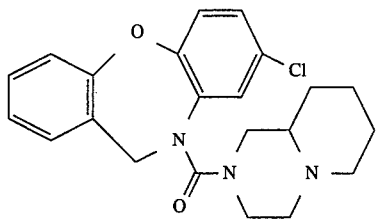

Methyl picolinate (300 g, 2.1 mole) and 3 g of its HCl salt were dissolved in 2 L of ethanol. To this solution heated to reflux with stirring, under $N_2$, was added a 2B ethanol solution (850 mL) of ethylene imine (120 g, 2.8 mole) over a 3 hour period. Following completion of addition, the reaction was refluxed overnight. The solvent was distilled off under vacuum and the residue was treated with acetone. After concentrating the solution, 88 g of hexahydro-2H-pyrido[1,2-a]pyrazin-1(6H)-one crystallized from the solution.

A sample of this lactam (168 g, 1.1 mole) dissolved in 2 L of dioxane was added to a refluxing solution of $LiAlH_4$ (40.0 g, 1.05 mole) in 1 L of dioxane over 2 hours. After refluxing the reaction overnight, it was cooled to room temperature and quenched with a mixture of 20% NaOH in dioxane. The resulting mixture was filtered through supercell and stripped of all solvent under reduced pressure. The residue was distilled to give 169 g of the desired octahydro-2H-pyrido[1,2-a]pyrazine.

The title compound of Example 2 (1.0 g, 3.4 mmol) was combined with octahydro-2H-pyrido[1,2-a]pyrazine (0.49 g, 3.5 mmol), triethylamine (0.41 g, 4.1 mmol), molecular sieve #3A (5 g), 60 mL of $CH_2Cl_2$, and 8 mL DMF. After stirring this mixture for 24 hours at room temperature and under a $N_2$ atmosphere, it was filtered and the solid was washed liberally with EtOAc and 1N potassium carbonate ($K_2CO_3$). The organic layer was separated from the filtrate, washed with 1N $K_2CO_3$ and brine. After removing all solvent under reduced pressure, the residue oil/glass (1.7 g) was chromatographed to yield 1.14 g of the title material.

Calculated for $C_{22}H_{24}N_3O_2Cl+0.125\ H_2O+0.05\ CH_2Cl_2$ (MW=404.41): C, 65.49; H, 6.07; N, 10.39; Cl, 9.64. Found: C, 65.49; H, 5.92; N, 10.29; Cl, 9.77.

Example 5

8-chloro-10,11-dihydro-10-[(octahydro-2H-pyrido[1,2-a]pyrazin-2-yl)carbonyl]dibenz[b,f][1,4]oxazepine hydrochloride

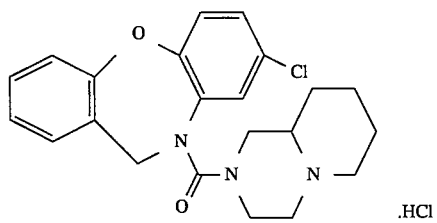

The title compound of Example 4 (1.0 g, 2.5 mmol) dissolved in 75 mL of $Et_2O$ was treated dropwise with 6.9 N hydrochloric acid (HCl) in dioxane until no further precipitation of solid was noted on the addition of further drops of HCl. The white solid was filtered, washed with $Et_2O$ and dried in vacuo. A 1.0 g sample of the white solid powder title product was obtained.

Calculated for $C_{22}H_{24}N_3O_2Cl+HCl+0.25\ H_2O$ (MW=438.87): C, 60.21; H, 5.86; N, 9.57; Cl, 16.16. Found: C, 60.01; H, 5.81; N, 9.41; Cl, 15.01.

Example 6

8-chloro-10,11-dihydro-10-[[4-(phenylmethyl)-1-piperazinyl]carbonyl]dibenz[b,f][1,4] oxazepine

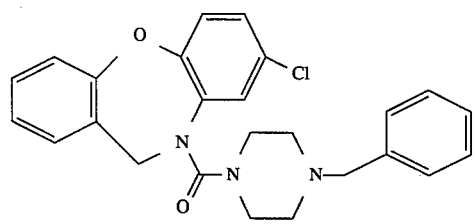

The title compound of Example 2 (1.0 g, 3.4 mmol) was combined with N-benzylpiperazine (0.60 g, 3.4 mmol) and the reaction was carried out by the method of Example 4. Following chromatographic separation, 1.4 g of the white solid title product was obtained.

Calculated for $C_{25}H_{24}N_3O_2Cl+0.05\ CH_2Cl_2$ (MW=438.19): C, 68.66; H, 5.54; N, 9.59; Cl, 8.90. Found: C, 68.60; H, 5.57; N, 9.49; Cl, 9.02.

Example 7

8-chloro-10,11-dihydro-10-[[4-(phenylmethyl)-1-piperazinyl]carbonyl]dibenz[b,f][1,4]oxazepine, monohydrochloride

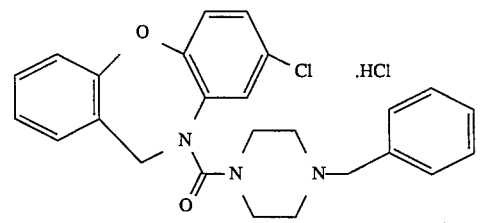

The title material was synthesized from the title material of Example 6 (1.30 g, 3.0 mmol) by the method of Example 5. A 1.32 g sample of the white solid title compound was obtained.

Calculated for $C_{25}H_{24}N_3O_2Cl+HCl+0.25\ H_2O$ (MW=474.90): C, 63.23; H, 5.41; N, 8.85; Cl, 14.93. Found: C, 63.25; H, 5.29; N, 8.75; Cl, 14.24.

Example 8

10-[(4-butyl-1-piperazinyl)carbonyl]-8-chloro-10,11-dihydrodibenz[b,f][1,4]oxazepine

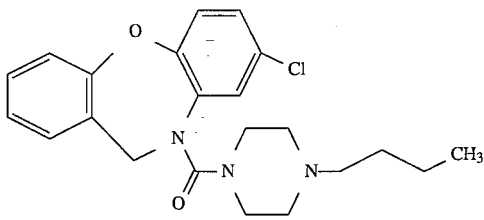

The title compound of Example 2 (1.0 g, 3.4 mmol) was combined with n-butyl-N-piperazine (0.48 g, 3.4 mmol) and the reaction was carried out by the method of Example 4. Following chromatographic separation, 1.22 g of the clear viscous oil title product was obtained.

Calculated for $C_{22}H_{26}N_3O_2Cl+0.05$ $CH_2Cl_2$ (MW=404.17): C, 65.53; H, 6.51; N, 10.40; Cl, 9.65. Found: C, 65.82; H, 6.67; N, 10.40; Cl, 11.07.

Example 9

10-[(4-butyl-1-piperazinyl)carbonyl]-8-chloro-10,11-dihydrodibenz[b,f][1,4]oxazepine, monohydrochloride

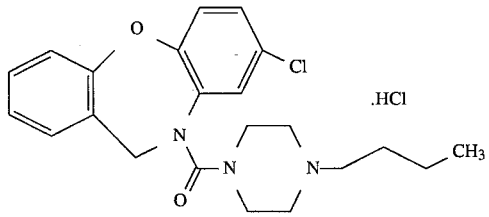

The title material was synthesized from the title material of Example 8 (1.12 g, 2.8 mmol) by the method of Example 5. A 1.11 g sample of the white solid title compound was obtained.

Calculated for $C_{22}H_{26}N_3O_2Cl+HCl+0.25$ $H_2O$ (MW=440.89): C, 59.93; H, 6.29; N, 9.58; Cl, 16.08. Found: C, 60.00; H, 6.18; N, 9.48; Cl, 15.47.

Example 10

8-chloro-10,11-dihydro-10-[[4-(2-pyridinyl)-1-piperazinyl]carbonyl]dibenz[b,f][1,4]oxazepine

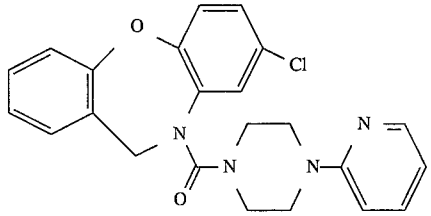

The title compound of Example 2 (1.0 g, 3.4 mmol) was combined with 1-(2-pyridyl)piperazine (0.56 g, 3.4 mmol) and the reaction was carried out by the method of Example 4. Following chromatographic purification, 1.16 g of the title product was obtained.

Calculated for $C_{23}H_{21}N_4O_2Cl+0.075$ $CH_2Cl_2+0.125$ $H_2O$ (MW=429.52): C, 64.53; H, 5.02; N, 13.04; Cl, 9.65. Found: C, 64.28; H, 5.05; N, 12.87; Cl, 9.43.

Example 11

8-chloro-10,11-dihydro-10-[[4-(2-pyridinyl)-1-piperazinyl]carbonyl]dibenz[b,f][1,4]oxazepine, monohydrochloride

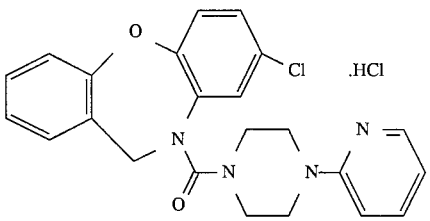

The title compound was synthesized from the title material of Example 10 (1.12 g, 2.8 mmol) by the method of Example 5. A 1.32 g sample of the white solid title compound was obtained.

Calculated for $C_{22}H_{26}N_3O_2Cl+HCl+0.25$ $H_2O$ (MW=440.89): C, 59.93; H, 6.29; N, 9.58; Cl, 16.08. Found: C, 60.00; H, 6.18; N, 9.48; Cl, 15.

Example 12

10-([1,4'-bipiperidin]-1'-ylcarbonyl)-8-chloro-10,11-dihydrodibenz[b,f][1,4]oxazepine

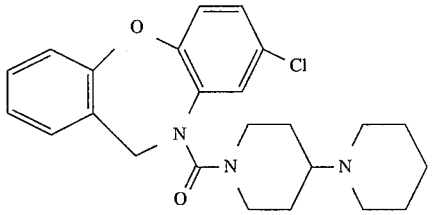

The title compound of Example 2 (0.6 g, 2.0 mmol) was combined with 1,4'-bipiperidine (0.38 g, 2.2 mmol) and the reaction was carried out by the method of Example 4. Following chromatographic purification, 0.74 g of the title product was obtained as a white solid.

Example 13

10-([1,4'-bipiperidin]-1'-ylcarbonyl)-8-chloro-10,11-dihydrodibenz[b,f][1,4]oxazepine, hydrochloride

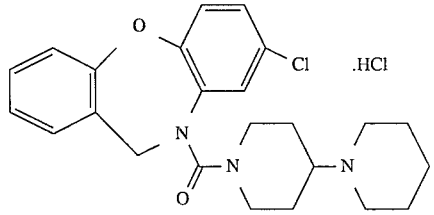

The title material was synthesized from the title material of Example 12 (0.70 g, 1.6 mmol) by the method of Example 5. A 0.50 g sample of the white solid title product was obtained.

Calculated for $C_{24}H_{28}N_3O_2Cl+0.9$ $HCl+0.5$ $H_2O$ (MW=467.78): C, 61.62; H, 6.44; N, 8.98; Cl, 14.40. Found: C, 61.65; H, 6.30; N, 8.94; Cl, 14.61.

Example 14

8-chloro-10-[(4-decyl-1-piperazinyl)carbonyl]-10,11-dihydrodibenz[b,f][1,4]oxazepine

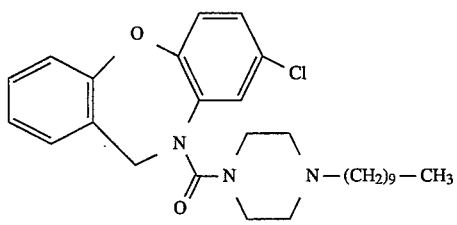

Ethyl 1-piperazinecarboxylate (77.3 g, 0.28 mole), 1-decanol methanesulfonate (77.3 g, 0.28 mole) from the condensation of 1-decanol with methane sulfonyl chloride, $K_2CO_3$ (39.0 g, 0.28 mole), and 500 mL of EtOH were combined and refluxed for 2 days under $N_2$. After cooling to room temperature, the reaction was partitioned between water and $Et_2O$. The organic layer was separated, washed 3 times with water, dried over $Na_2SO_4$ and stripped of all solvent under reduced pressure to yield the crude product oil. Chromatographic purification of the crude oil gave 53.4 g of ethyl 4-decyl-1-piperazinecarboxylate.

Ethyl 4-decyl-1-piperazinecarboxylate (53.4 g, 0.18 mole) in 300 mL of concentrated HCl was refluxed for 2 days under $N_2$. After all of the solvent was removed under reduced pressure and the residue was suspended in ethanol, the product 1-decylpiperazine hydrochloride (20.2 g) was filtered off and dried. This material was converted to its free base, 1-decylpiperazine, by treatment with NaOH.

The title compound of Example 2 (1.0 g, 3.4 mmol) was combined with 1-decylpiperazine (0.77 g, 3.4 mmol) and the reaction was carried out by the method of Example 4. Following chromatographic purification, 1.08 g of the title product was obtained.

Example 15

8-chloro-10-[(4-decyl-1-piperazinyl)carbonyl]-10,11-dihydrodibenz[b,f][1,4]oxazepine, monohydrochloride

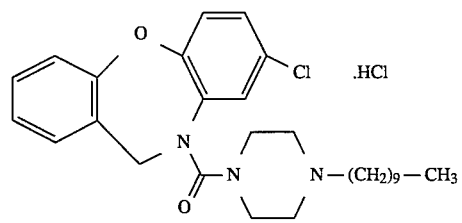

The title compound was synthesized from the title material of Example 14 (0.91 g, 1.9 mmol) by the method of Example 5. A 0.87 g sample of the white solid title product was obtained.

Calculated for $C_{28}H_{38}N_3O_2Cl+HCl+0.5\ H_2O$ (MW=520.54): C, 64.61; H, 7.55; N, 8.07; Cl, 13.62. Found: C, 64.41; H, 7.53; N, 8.03; Cl, 13.36.

Example 16

8-chloro-10,11-dihydro-10-[(4-propyl-1-piperazinyl)carbonyl]dibenz[b,f][1,4]oxazepine

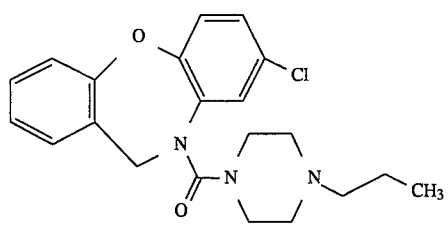

By the methods of Example 14, ethyl 1-piperazinecarboxylate was reacted with the methanesulfonate of n-propanol and the product, ethyl 4-propyl-1-piperazinecarboxylate, was converted to 1-propylpiperazine.

The title compound of Example 2 (1.0 g, 3.4 mmol) was combined with 1-propylpiperazine (0.44 g, 3.4 mmol) and the reaction was carried out by the method of Example 4. Following chromatographic purification, 1.16 g of the title product was obtained as a white solid.

Example 17

8-chloro-10,11-dihydro-10-[(4-propyl-1-piperazinyl)carbonyl]dibenz[b,f][1,4]oxazepine, hydrochloride

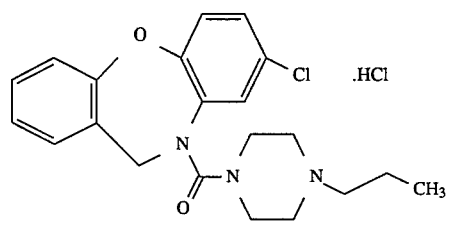

The title compound was synthesized from the title material of Example 16 (1.11 g, 2.9 mmol) by dissolving it in 28 mL of 2N HCl in methanol (MeOH). After stirring this solution for 30 minutes, all solvent was removed under reduced pressure. The resulting residue was washed with $Et_2O$, dissolved in water, treated with activated charcoal, filtered and lyophilized. An 0.80 g sample of the pale green solid title product was obtained.

Calculated for $C_{21}H_{24}N_3O_2Cl+1.1\ HCl+0.75\ H_2O$ (MW= 439.51): C, 57.39; H, 6.10; N, 9.56; Cl, 16.94. Found: C, 57.69; H, 5.83; N, 9.58; Cl, 17.26.

Example 18

8-chloro-10-[(4-ethyl-1-piperazinyl)carbonyl]-10,11-dihydrodibenz[b,f][1,4]oxazepine

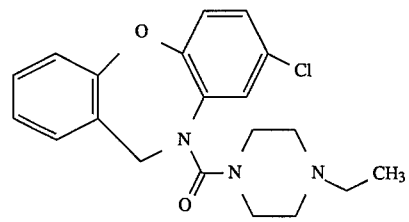

The title compound of Example 2 (1.0 g, 3.4 mmol) was combined with 4-ethylpiperazine (0.43 g, 3.7 mmol) and the reaction was carried out by the method of Example 4. Following chromatographic purification, 1.10 g of the title product was obtained as a pale yellow solid.

Example 19

8-chloro-10-[(4-ethyl-1-piperazinyl)carbonyl]-10,11-dihydrodibenz[b,f][1,4]oxazepine, hydrochloride

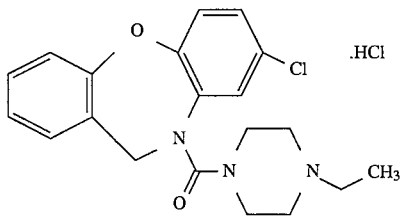

The title compound was synthesized from the title material of Example 18 (0.99 g, 2.7 mmol) by the method of Example 17. An 0.93 g sample of the pale yellow solid title product was obtained.

Calculated for $C_{20}H_{22}N_3O_2Cl+1.1$ HCl+0.5 $H_2O$ (MW= 420.98): C, 57.06; H, 5.77; N, 9.98; Cl, 17.69. Found: C, 57.11; H, 5,58; N, 10.03; Cl, 17.79.

Example 20

1,1-dimethylethyl 4-[(8-chlorodibenz[b,f][1,4]oxazepin-10(11H)-yl)carbonyl]-1-piperazinecarboxylate

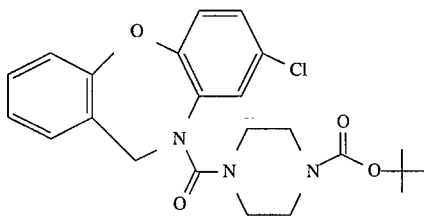

The title compound of Example 2 (1.0 g, 3.4 mmol) was combined with 1,1-dimethylethyl 1-piperazinecarboxylate (0.44 g, 3.4 mmol) and the reaction was carried out by the method of Example 3. Following chromatographic purification, 1.16 g of the title product was obtained as a white solid.

Calculated for $C_{23}H_{226}N_3O_4Cl+0.1$ $CH_2Cl_2$ (MW=452.42): C, 61.33; H, 5.84; N, 9.40; Cl, 9.40. Found: C, 61.26; H, 5,90; N, 9.15; Cl, 9.09.

Example 21

8-chloro-10,11-dihydro-10-[[4-(1-methylethyl)-1-piperazinyl]carbonyl]dibenz[b,f] [1,4]oxazepine

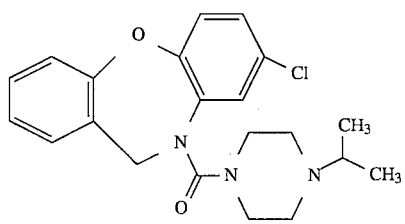

Ethyl 1-piperazinecarboxylate (60.0 g, 0.3 mole), 2-bromopropane (73.8 g, 0.6 mole), $K_2CO_3$ (82.8 g, 0.6 mole), and 600 mL of EtOH were combined and refluxed for overnight. After cooling to room temperature, all solvent was removed under reduced pressure. The residue was dissolved in 200 mL of water and extracted with 2×250 mL of $Et_2O$. The organic layer was separated, dried, and the ethyl 4-(1-methylethyl)-1-piperazinecarboxylate product was precipitated as its HCl salt by treatment of the $Et_2O$ layer with HCl/isopropanol. The product HCl salt was filtered, washed with $Et_2O$, and dried (76 g).

After the preceding material (76 g), dissolved in 500 mL of concentrated HCl was refluxed overnight, all solvent was removed under reduced pressure. The residue product oil was treated with EtOH. The crystalline 1-(1-methylethyl)piperazine dihydrochloride salt was filtered, washed with $Et_2O$, and dried.

This material was converted to its free base by treatment with 50% aqueous NaOH and extraction with $Et_2O$. After drying the organic layer, all solvent was stripped and the residue was distilled at atmospheric pressure to give 22.1 g of 1-(1-methylethyl)piperazine (b.p.=168°–170° C.).

The title compound of Example 2 (1.0 g, 3.4 mmol) was combined with 1-(1-methylethyl)piperazine (0.48 g, 3.7 mmol) and the reaction was carried out by the method of Example 4. Following chromatographic purification, 1.17 g of the title product was obtained as a white solid.

Example 22

8-chloro-10,11-dihydro-10-[[4-(1-methylethyl)-1-piperazinyl]carbonyl]dibenz[b,f][1,4]oxazepine, hydrochloride

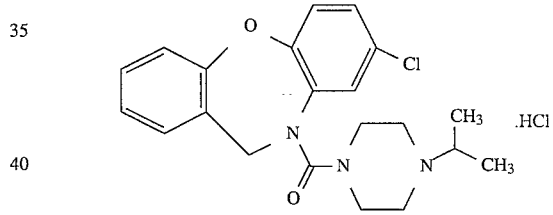

The title compound was synthesized from the title material of Example 21 (0.99 g, 2.7 mmol) by the method of Example 17. A 0.93 g sample of the pale yellow solid title product was obtained.

Calculated for $C_{21}H_{24}N_3O_2Cl+1.1$ HCl+0.3 $H_2O$ (MW= 431.40): C, 58.47; H, 6.00; N, 9.74. Found: C, 58.52; H, 6.06; N, 9.78.

Example 23

8-chloro-10,11-dihydro-10-[(hexahydro-4-methyl-1H-1,4-diazepin-1-yl)carbonyl]dibenz[b,f][1,4]oxazepine

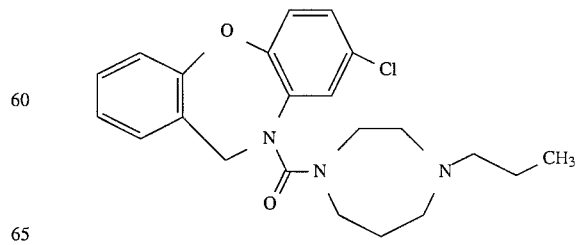

A mixture of the product of Example 96 (37.0 g, 0.21 mole), n-propyl tosylate (68.1 g, 0.31 mole), Na₂CO₃ (16.8 g, 0.16 mole), and 160 mL of EtOH were refluxed for 14 hours under N₂. After cooling the reaction, it was filtered and all solvent was removed from the filtrate under reduced pressure. The residue was mixed with 300 mL of water and extracted with 2×200 mL of Et₂O. The product HCl salt was precipitated and converted to hexahydro-1-propyl-1H-1,4-diazacycloheptane by the methods of Example 21.

The title compound of Example 2 (1.0 g, 3.4 mmol) was combined with hexahydro-1-propyl-1H-1,4-diazacycloheptane (0.53 g, 3.7 mmol) and the reaction was carried out by the method of Example 4. Following chromatographic purification, 1.20 g of the title product was obtained as a pale yellow oil.

Example 24

8-chloro-10,11-dihydro-10-[(hexahydro-4-methyl-1H-1,4-diazepin-1-yl)carbonyl]dibenz[b,f][1,4]oxazepine, monohydrochloride

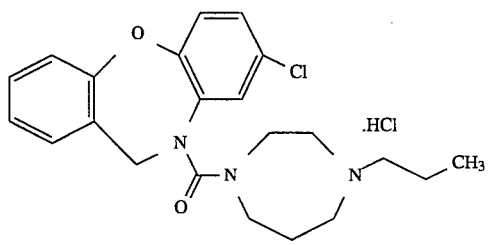

The title compound was synthesized from the title material of Example 23 (0.99 g, 2.7 mmol) by the method of Example 17. A 1.13 g sample of the solid title product was obtained.

Calculated for C₂₂H₂₆N₃O₂Cl+1 HCl+0.4 H₂O (MW= 443.59): C, 59.57; H, 6.32; N, 9.47; Cl, 15.98. Found: C, 59.48; H, 6.32; N, 9.45; Cl, 16.14.

Example 25

8-chloro-10,11-dihydro-10-(1-piperazinylcarbonyl)dibenz[b,f][1,4]oxazepine, monohydrochloride

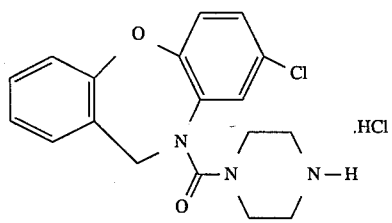

The title compound of Example 20 (5.0 g, 11.1 mmol) was dissolved in 40 mL of acetic acid (HOAc). This homogeneous solution was then treated with 16 mL of 6.9N HCl dissolved in dioxane. After stirring this mixture for 1 hour, all solvent was removed under reduced pressure. The residue was dissolved in MeOH, stripped of all solvent, triturated with Et₂O, filtered, washed with Et₂O and dried in vacuo to provide 3.90 g of the white solid title salt.

Calculated for C₁₈H₁₈N₃O₂Cl+1 HCl+1.0 H₂O+0.025 Et₂O (MW=416.82): C, 54.75; H, 5.68; N, 10.08; Cl, 17.01. Found: C, 54.57; H, 5.35; N, 10.01; Cl, 16.85.

Example 26

1,1-dimethylethyl 4-(4-pyridinylcarbonyl)-1-piperazinecarboxylate

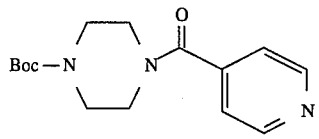

A sample of 4-pyridinecarboxylic acid (1.32 g, 10.7 mmol) was dissolved in 50 mL of CH₂Cl₂. To this solution under N₂ was added N-methylmorpholine (1.21 mL, 11.0 mmol) before it was cooled to −78° C. and isobutylchloroformate (1.39 mL, 10.7 mmol) was added. The reaction was allowed to warm to 0° C. and stirred at this temperature for 30 minutes before it was cooled again to −78° C. and t-butyloxycarbonyl piperazine (2.0 g, 10.7 mmol) was added. The mixture was allowed to warm to room temperature and stirred for 18 hours. All solvent was removed under reduced pressure to give a residue that was dissolved in EtOAc, washed with saturated NaHCO₃ and brine, and dried (Na₂SO₄). After all solvent was removed in vacuo, the residue was chromatographed to generate 1.3 g of the title compound.

Example 27

1-(4-pyridinylcarbonyl)piperazine

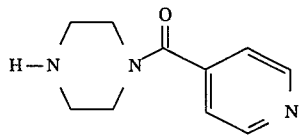

The title material was synthesized from the title product of Example 26 (1.3 g, 4.46 mmol) by the method described in Example 25, except that the title free base was generated by treatment of its HCl salt with 0.5N K₂CO₃ in CH₂Cl₂. The CH₂Cl₂ solution was dried over Na₂SO₄ and all solvent removed under reduced pressure to provide 333 mg of the title free base. This material was used without further purification.

Example 28

1-[(8-chlorodibenz[b,f][1,4]oxazepin-10(11H)-yl)carbonyl]-4-(4-pyridinylcarbonyl)piperazine

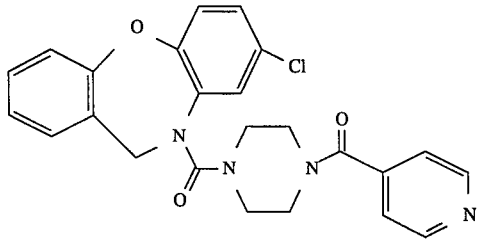

The title compound of Example 2 (0.51 g, 1.7 mmol) was reacted with the title product of Example 27 (0.33 g, 1.7 mmol) by the method of Example 4. Following chromatographic purification, 0.16 g of the title product was obtained.

Example 29

1-[(8-chlorodibenz[b,f][1,4]oxazepin-10(11H)-yl)carbonyl]-4-(4-pyridinylcarbonyl)piperazine, monohydrochloride

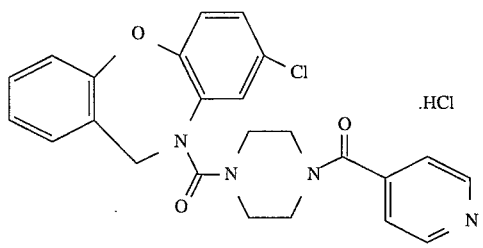

The title product of Example 28 was dissolved in 10 mL of MeOH. Excess 6.9N HCl dioxane was added to the solution. After stirring this solution for 30 minutes, all solvent was removed under reduced pressure. The residue was dissolved in water/MeOH and lyophilized to produce 0.11 g of the title product as a granular white solid.

Calculated for $C_{24}H_{21}N_4O_3Cl+1$ HCl+0.8 $H_2O$ (MW=499.78): C, 57.68; H, 4.76; N, 11.21; Cl, 14.19. Found: C, 57.49; H, 4.36; N, 10.93; Cl, 13.91.

Example 30

1,1-dimethylethyl 4-[1-oxo-3-(3-pyridinyl)propyl]-1-piperazinecarboxylate

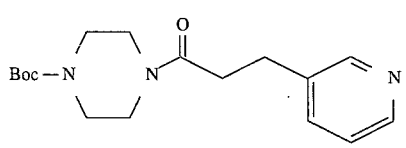

A sample of 3-pyridinepropanoic acid (0.1 g, 0.7 mmol) was reacted with t-butyloxycarbonyl piperazine (0.19 g, 1.0 mmol) by the method of Example 26 to produce 95 mg of the white solid title compound after chromatography.

Example 31

1-[3-(3-pyridinyl)-1-oxopropyl]piperazine

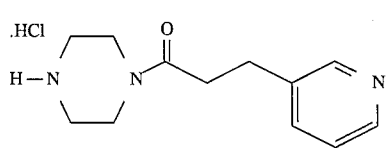

The title product of Example 30 (95.0 mg, 0.30 mmol) was dissolved in 6 mL of HOAc. To this solution was added 0.5 mL of 6N HCl in dioxane. After stirring this solution for 25 minutes, all solvent was removed under reduced pressure to give 76 mg of the title product.

Example 32

1-[(8-chlorodibenz[b,f][1,4]oxazepin-10(11H)-yl)carbonyl]-4-[(1-oxo-3(3-pyridinyl)propyl]piperazine

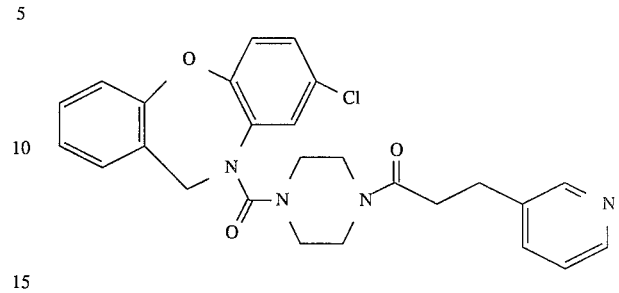

The title compound of Example 2 (0.51 g, 1.7 mmol) was reacted with the title product of Example 31 (0.076 g, 0.30 mmol) by the method of Example 4, except that an additional 1.7 mmol of $Et_3N$ was used to neutralize the HCl salt of the title compound of Example 4. Following chromatographic purification, 0.11 g of the title product was obtained.

Example 33

1-[(8-chlorodibenz[b,f][1.4]oxazepin-10(11H)-yl)carbonyl]-4-[1-oxo-3(3-pyridinyl)propyl]-piperazine, monohydrochloride

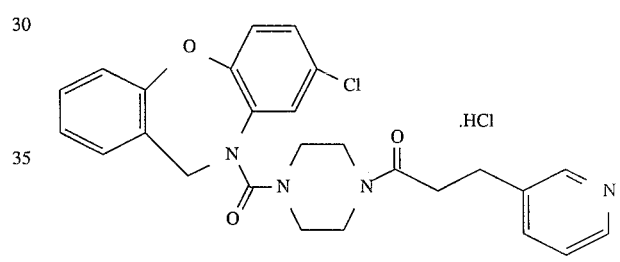

The title product of Example 32 (0.1 g, 0.21 mmol) was converted to the title compound by the method of Example 29. A 96 mg sample of this white solid salt was obtained.

Calculated for $C_{26}H_{25}N_4O_3Cl+1$ HCl+1.25 $H_2O$ (MW=535.94): C, 58.27; H, 5.36; N, 10.45; Cl, 13.23. Found: C, 58.12; H, 4.85; N, 10.34; Cl, 13.27.

Example 34

8-chloro-10,11-dihydro-10-[[4-(1-pyrrolidinyl)-1-piperidinyl]carbonyl]dibenz[b,f][1,4]oxazepine

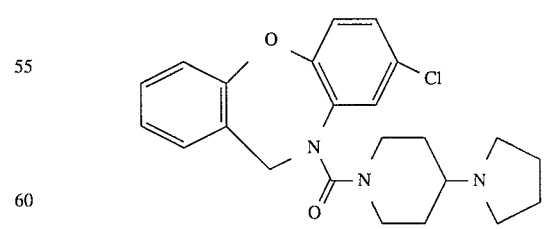

The title compound of Example 2 (1.0 g, 3.4 mmol) was reacted with 4-(1-pyrrolidinyl)piperidine (0.77 g, 3.4 mmol) and the reaction was carried out by the method of Example 4. Following chromatographic purification, 0.91 g of the title product was obtained.

Example 35

8-chloro-10,11-dihydro-10-[[4-(1-pyrrolidinyl)-1-piperidinyl]carbonyl]dibenz[b,f][1,4]oxazepine, hydrochloride

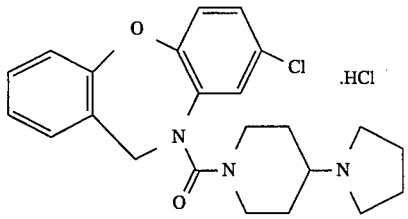

The title product of Example 34 (0.90 g, 2.17 mmol) was converted to the title compound by the method of Example 29. A 0.55 g sample of this title white solid salt product was obtained.

Calculated for $C_{23}H_{26}N_3O_2Cl+1.1$ HCl+1 $H_2O$ (MW= 470.05): C, 58.77; H, 6.24; N, 8.94; Cl, 15.84. Found: C, 58.74; H, 5.53; N, 8.87; Cl, 15.56.

Example 36

1,1-dimethylethyl 4-(2-furanylcarbonyl)-1-piperazinecarboxylate

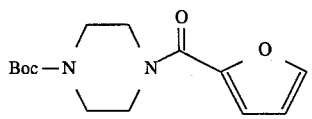

t-Butyloxycarbonyl piperazine (2.0 g, 10.7 mmol) was reacted with furancarbonyl chloride (1.40 g, 10.7 mmol) by the method of Example 4. Following chromatography, a 2.25 g sample of the title compound was obtained.

Example 37

1-(2-furanylcarbonyl)piperazine hydrochloride

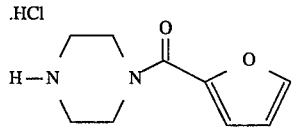

The title compound of Example 36 (2.25 g, 14.4 mmol) was converted to the title product by the method of Example 31. A 1.4 g sample of this material was obtained.

Calculated for $C_9H_{12}N_2O_2Cl+1$ HCl (MW=216.67): C, 49.89; H, 6.05; N, 12.93; Cl, 16.36. Found: C, 49.79; H, 6.11; N, 12.82; Cl, 16.24.

Example 38

1-[(8-chlorodibenz[b,f][1,4]oxazepin-10(11H)-yl)carbonyl]-4-(2-furanylcarbonyl)piperazine

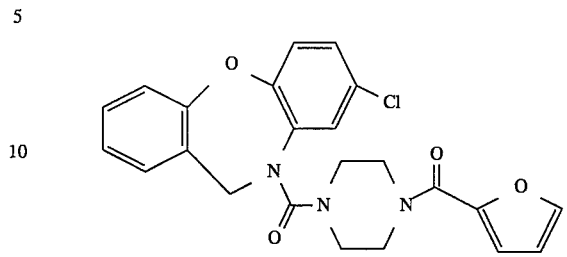

The title compound of Example 2 (1.0 g, 3.4 mmol) was reacted with the title compound of Example 37 (0.76 g, 3.5 mmol), and the reaction was carried out by the method of Example 4 with the modification of Example 32. Following chromatographic purification, 1.10 g of the title product was obtained as a white solid.

Calculated for $C_{23}H_{20}N_3O_4Cl+0.375$ $H_2O+0.1$ $CH_2Cl_2$ (MW=453.13): C, 49.89; H, 6.05; N, 12.93; Cl, 16.36. Found: C, 49.79; H, 6.11; N, 12.82; Cl, 16.24.

Example 39

COMPOUND A 8-chloro-10,11-dihydro-10-[[4-(2-phenylethyl)-1-piperazinyl]carbonyl]dibenz[b,f][1,4]oxazepine

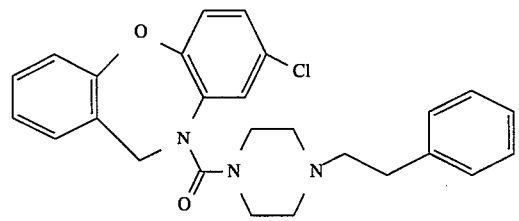

COMPOUND B 10,11-dihydro-10-[[4-(2-phenylethyl)-1-piperazinyl]carbonyl]dibenz[b,f][1,4]oxazepine

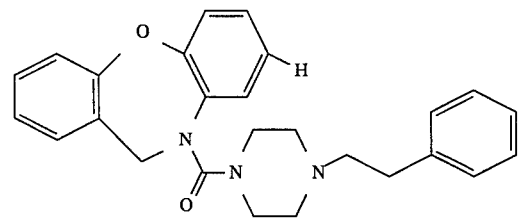

The title compound of Example 25 (1.0 g, 2.6 mmol), phenylacetaldehyde (0.40 g, 3.3 mmol), triethylamine (0.32 g, 3.2 mmol), 40 mL of EtOH triethylamine, and 5% Palladium on carbon were combined in a standard Parr hydrogenation shaker. This mixture was shaken under a hydrogen ($H_2$) atmosphere of 5 psi at room temperature for 9 hours. An uptake in $H_2$ of 9.03 psi was observed. The reaction mixture was filtered and the filtrate was stripped of solvent under reduced pressure before it was dissolved in EtOAc (500 mL). This solution was washed with 1×75 mL of 0.5N $K_2CO_3$ and 2×75 mL of brine before it was dried ($Na_2SO_4$) and all solvent removed in vacuo. The residue was chromatographed to yield two white solid products; title COMPOUND A (0.75 g) and title COMPOUND B (0.15 g). COMPOUND A has a greater Rf than COMPOUND B when a thin layer chromatograph (TLC) on silica gel plates eluting with solvent system of 40% EtOAC/hexane containing 0.05% $NH_4OH$ is performed.

COMPOUND A:

Calculated for $C_{26}H_{26}N_3O_2Cl$ (MW=447.96): C, 69.71; H, 5.85; N, 9.38; Cl, 7.91. Found: C, 69.71 H, 5.74; N, 9.36; Cl, 7.75.

COMPOUND B:

Calculated for $C_{26}H_{27}N_3O_2+0.5\ H_2O$ (MW=422.53): C, 73.91; H, 6.68; N, 9.95. Found: C, 74.08; H, 6.56; N, 9.89.

Example 40

8-chloro-10,11-dihydro-10-[[4-(2-phenylethyl)-1-piperazinyl]carbonyl]dibenz[b,f][1,4]oxazepine, monohydrochloride

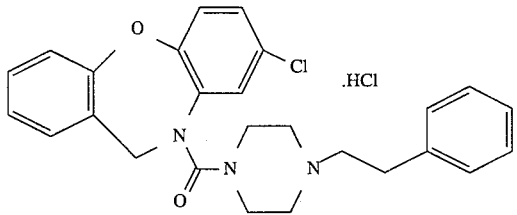

The title compound was synthesized from a title material of Example 39 (COMPOUND A) (0.60 g, 1.3 mmol) by the method of Example 5. A 0.64 g sample of the white solid title compound was obtained.

Calculated for $C_{26}H_{26}N_3O_2Cl+HCl$ (MW=497.94): C, 62.72; H, 5.77; N, 8.44; Cl, 14.24. Found: C, 62.69 H, 5.55; N, 8.51; Cl, 13.57.

Example 41

10,11-dihydro-10-[[4-(2-phenylethyl)-1-piperazinyl]carbonyl]dibenz[b,f][1,4]oxazepine, monohydrochloride

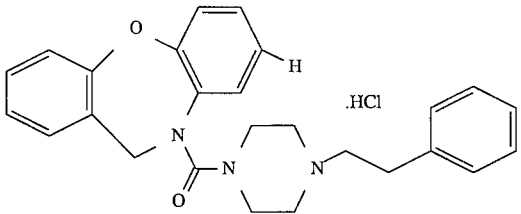

The title compound was synthesized from a title material of Example 39 (COMPOUND B) (0.10 g, 0.2 mmol) by the method of Example 5. A 0.07 g sample of the white solid title compound was obtained.

Calculated for $C_{22}H_{27}N_3O_2+HCl+0.25\ H_2O$ (MW=454.49): C, 68.71; H, 6.32; N, 9.25; Cl, 7.80. Found: C, 68.71; H, 6.18; N, 9.48; Cl, 15.47.

Example 42

8-chloro-10,11-dihydro-10-[(4-phenyl-1-piperazinyl)carbonyl]dibenz[b,f][1,4]oxazepine, hydrochloride

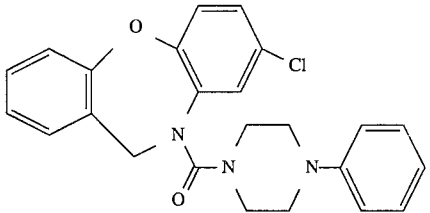

The title compound of Example 2 (1.25 g, 4.25 mmol) was combined with N-phenylpiperazine (0.73 g, 4.5 mmol) and the reaction was carried out by the method of Example 4. Following chromatographic separation, 1.7 g of the white solid title product was obtained.

Calculated for $C_{24}H_{22}N_3O_2Cl+0.01\ CH_2Cl_2$ (MW=428.41): C, 67.57; H, 5.22; N, 9.81; Cl, 9.83. Found: C, 67.47; H, 5.30; N, 9.75; Cl, 9.59.

Example 43

8-chloro-10,11-dihydro-10-[(4-phenyl-1-piperazinyl)carbonyl]dibenz[b,f][1,4]oxazepine, hydrochloride

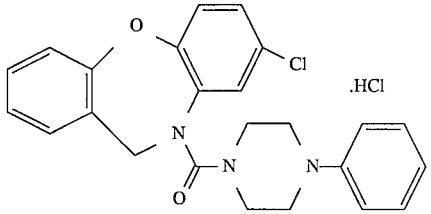

The title material was synthesized from the title material of Example 42 (1.55 g 3.0 mmol) by the method of Example 5. A 1.67 g sample of the white solid title compound salt was obtained.

Calculated for $C_{24}H_{22}N_3O_2Cl+0.7\ HCl+0.125\ H_2O$ (MW=447.69): C, 64.39; H, 5.17; N, 9.39; Cl, 13.46. Found: C, 64.26; H, 5.15; N, 9.33; Cl, 13.22.

Example 44

1,1-dimethylethyl 4-(3-thienylmethyl)-1-piperazinecarboxylate

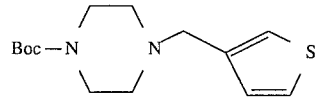

A sample of t-butyloxycarbonyl piperazine (1.0 g, 5.4 mmol) was dissolved in 10 mL of MeOH. 3-thiophenylcarboxaldehyde (0.72 g, 6.4 mmol) was added to the stirred homogeneous solution maintained under an argon atmosphere and at room temperature. After stirring for 10 minutes, sodium cyanoborohydride (0.68 g, 10.8 mmol) was added to the solution, and this mixture was allowed to stir for 48 hours. To this mixture was added 20 mL of 6N HCl. Following cessation of gas evolution (20 minutes) the reaction mixture was partitioned between water and $Et_2O$. The $Et_2O$ was separated and the aqueous was brought to pH 10.5 with NH$_4$OH. The aqueous layer was extracted with 3×100 mL of EtOAc. The crude title product was isolated by drying the EtOAc solution over Na$_2$SO$_4$ and removing the solvent under reduced pressure. This material was used in subsequent reactions without further purification.

Example 45

1-(3-thienylmethyl)-1-piperazine, monohydrochloride

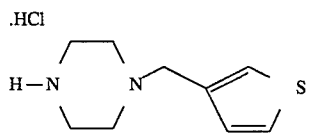

The title compound of Example 44 (0.58 g, 2.0 mmol) was converted to the title product by the method of Example 31. A 0.35 g sample of this material was obtained.

Example 46

8-chloro-10,11-dihydro-10-[[4-(3-thienylmethyl)-1-piperazinyl]carbonyl]dibenz[b,f][ 1,4]oxazepine

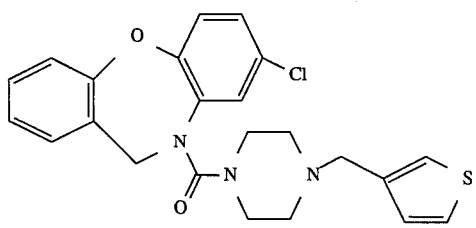

The title compound of Example 2 (0.57 g, 1.90 mmol) was combined with the title product of Example 45 (0.35 g, 1.90 mmol) and the reaction was carried out by the method of Example 4 with the modification of Example 32. Following chromatographic separation, 1.7 g of the white solid title product was obtained.

Calculated for C$_{23}$H$_{22}$N$_3$O$_2$SCl+0.05 CH$_2$Cl$_2$ (MW=444.21): C, 62.32; H, 5.01; N, 9.46; S, 7.22; Cl, 8.78. Found: C, 62.34; H, 5.13; N, 9.30; S, 7.38; Cl, 8.70.

Example 47

8-chloro-10,11-dihydro-10-[[4-(3-thienylmethyl)-1-piperazinyl]carbonyl]dibenz[b,f][1,4]oxazepine, monohydrochloride

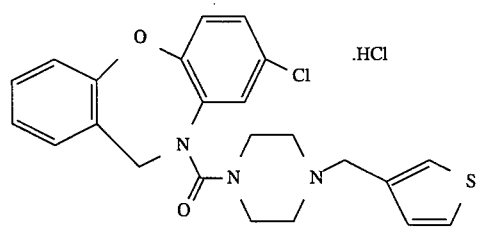

The title material was synthesized from the title material of Example 46 (0.24 g, 3.0 mmol) by the method of Example 5. A 0.21 g sample of the white solid title compound salt was obtained.

Calculated for C$_{23}$H$_{22}$N$_3$O$_2$SCl+HCl (MW=476.25): C, 57.98; H, 4.87; N, 8.82; S, 6.73; Cl, 14.88. Found: C, 58.29; H, 4.92; N, 8.89; S, 6.46; Cl, 13.90.

Example 48

8-chloro-10,11-dihydro-10-[[2-[2-(1-pyrrolidinyl)ethyl]-1-piperidinyl]carbonyl] dibenz[b,f][1,4]oxazepine

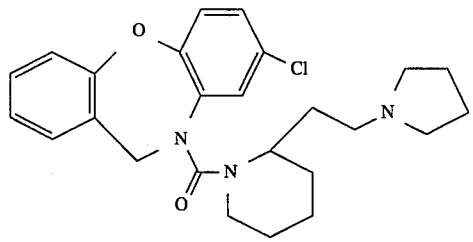

The title compound of Example 2 (1.25 g, 4.25 mmol) was combined with 2-(2-pyrrolidinoethyl)piperadine (0.82 g, 4.50 mmol) and the reaction was carried out by the method of Example 4. Following chromatographic separation, 0.41 g of the white solid title product was obtained.

Calculated for C$_{25}$H$_{30}$N$_3$O$_2$Cl+0.1 CH$_2$Cl$_2$+0.5 H$_2$O (MW=457.49): C, 65.90; H, 6.87; N, 9.19; Cl, 9.30. Found: C, 66.19; H, 6.72; N, 9.14; Cl, 9.44.

Example 49

8-chloro-10,11-dihydro-10-[[2-[2-(1-pyrrolidinyl)ethyl]-1-piperidinyl]carbonyl]dibenz[b,f][1,4]oxazepine, hydrochloride

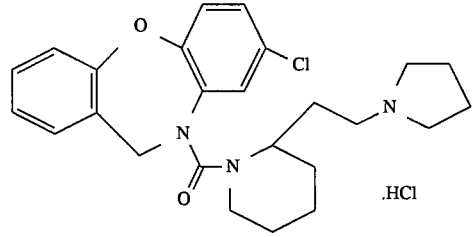

The title material was synthesized from the title material of Example 48 (0.24 g, 3.0 mmol) by the method of Example 5. A 0.21 g sample of the white solid title compound salt was obtained.

Calculated for C$_{25}$H$_{30}$N$_3$O$_2$Cl+1.1 HCl+1.5 H$_2$O (MW= 507.12): C, 59.21; H, 6.78; N, 8.29; Cl, 8.29. Found: C, 59.11; H, 6.44; N, 8.09; Cl, 14.92.

Example 50 ethyl 4-[(8-chlorodibenz[b,f][1,4]oxazepin-10(11H)-yl)carbonyl]-1-phenyl-2-piperazinecarboxylate

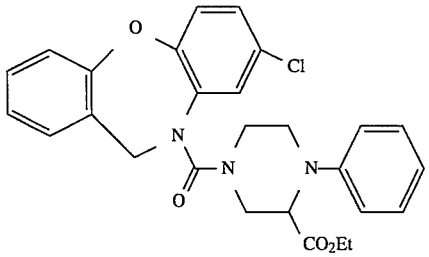

N-phenylethylenediamine (24.4 g, 0.18 mole) and benzylaldehyde (19.1 g, 0.18 mole) were mixed neat, let stand for 1 hour, diluted with Et₂O, and dried over Na₂SO₄. Removal of the solvent under reduced pressure gave 34.5 g of N-phenyl-N'-phenylmethylenyl-1,2-ethanediamine.

To a 5.0 g (22.3 mmol) sample of this material dissolved in 80 mL of ethanol was added 3.0 g of NaBH₄ (78.9 mmol) portionwise to the stirred reaction. After 3 hours at room temperature, all solvent was stripped under reduced pressure and the residue was dissolved in dilute HCl. This mixture was filtered and the filtrate was made basic with dilute NaOH before extracting with Et₂O. This extract was dried over Na₂SO₄ and stripped of all solvent to provide 3.9 g of the desired N-phenyl-N'-(phenylmethyl)-1,2-ethanediamine.

A mixture of this ethylenediamine (31 g, 0.137 mole) and triethylamine (28 g, 0.277 mole) was added dropwise over 30 minutes to a stirred solution of ethyl-2,3-dibromopropionate (35.0 g, 0.135 mole) dissolved in 200 mL of toluene and heated to 40° C. After the addition was complete, the reaction was heated at 80°–85° C. for 7 hours, cooled to room temperature, and partitioned between water and toluene. The organic layer was separated, dried, and stripped of all solvent under reduced pressure to yield 38 g of the crude product. Chromatographic purification gave 12.8 g of ethyl 1-phenyl-4-(phenylmethyl)-2-piperazinecarboxylate.

An EtOH (75 mL) solution of ethyl 1-phenyl-4-(phenylmethyl)-2-piperazinecarboxylate (2.20 g, 6.8 mmol) and 500 mg of 4% Pd/C was subjected to hydrogenolysis in a standard Parr apparatus. The reaction was carried out for 10 hours at 55° C. and under a hydrogen pressure of 5 psi. After the catalyst was removed by filtration and the solvent by stripping under reduced pressure, 1.5 g of ethyl 1-phenyl-2-piperazinecarboxylate was obtained as a clear oil.

The title compound of Example 2 (1.8 g, 6.30 mmol) was reacted with ethyl 1-phenyl-2-piperazinecarboxylate (0.82 g, 4.50 mmol) by the method of Example 4. Following chromatographic separation, 2.66 g of the white solid title product was obtained.

Calculated for C₂₇H₂₆N₃O₄Cl+0.5 CH₂Cl₂ (MW=496.22): C, 65.47; H, 5.30; N, 8.47; Cl, 7.86. Found: C, 65.27; H, 5.18; N, 8.48; Cl, 7.94.

Example 51

1,1-dimethylethyl 4-(2-thienylmethyl)-1-piperazinecarboxylate

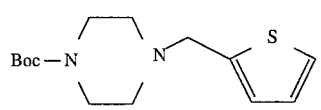

The title material was synthesized from t-butyloxycarbonyl piperazine (1.0 g, 5.4 mmol) and 2-thiophenylcarboxaldehyde (0.72 g, 6.4 mmol) by the method of Example 44. A 0.56 g sample of the crude title material was obtained and used without further purification.

Example 52

1-(2-thienylmethyl)piperazine, monohydrochloride

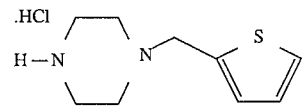

The title compound of Example 51 (0.56 g, 2.0 mmol) was converted to the title product by the method of Example 31. A 0.57 g sample of this material was obtained.

Example 53

8-chloro-10,11-dihydro-10-[[4-(2-thienylmethyl)-1-piperazinyl]carbonyl]dibenz[b,f] [1,4]oxazepine

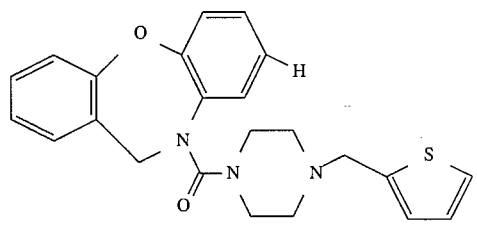

The title compound of Example 2 (0.93 g, 3.20 mmol) was reacted with the product of Example 52 (0.57 g, 3.20 mmol) by the method of Example 4 with the modification described in Example 32. Following chromatographic separation, 0.26 g of the white solid title product was obtained.

Calculated for C₂₃H₂₂N₃O₂SCl (MW=439.96): C, 62.79; H, 5.04; N, 9.55; S, 7.29; Cl, 8.06. Found: C, 62.67; H, 5.22; N, 9.50; S, 6.75; Cl, 8.06.

Example 54

8-chloro-10,11-dihydro-10-[[4-(2-thienylmethyl)-1-piperazinyl]carbonyl]dibenz[b,f] [1,4]oxazepine, monohydrochloride

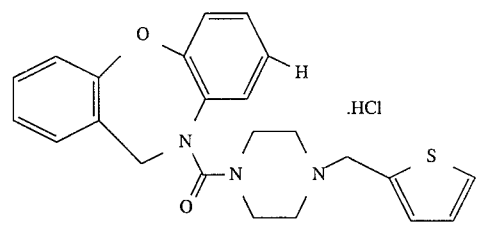

The title material was synthesized from the title material of Example 53 (0.24 g, 3.0 mmol) by the method of Example 5. A 0.21 g sample of the white solid title compound salt was obtained.

Calculated for C₂₃H₂₂N₃O₂SCl+HCl 3/8 H₂O (MW= 483.18): C, 57.17; H, 4.95; N, 8.57; S, 6.64; Cl, 14.67. Found: C, 57.27; H, 4.90; N, 8.70; S, 6.64; Cl, 13.97.

Example 55

1-[(8-chlorodibenz[b,f][1,4]oxazepin-10(11H)-yl)carbonyl]-4-(3-pyridinylacetyl)piperazine

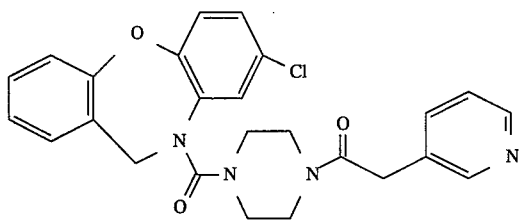

The title compound of Example 25 (1.5 g, 3.8 mmol) and 1-(3-pyridinylacetyl)piperazine (0.67 g, 3.8 mmol) were dissolved in 20 mL of DMF. To this magnetically stirred homogeneous solution cooled to −5° C. under an argon atmosphere were added 1-(3-dimethylaminopropyl)-3-ethylcarbodiimide hydrochloride (0.73 g, 3.8 mmol), 1-hydroxy benzotriazole hydrate (0.51 g, 3.8 mmol) and triethyl amine (1.15 g, 11.4 mmol). The reaction mixture was allowed to slowly warm to room temperature and stirred an additional 16 hours before all solvent was removed under reduced pressure. The residue was dissolved in EtOAc (300 mL) and this solution was washed with 2×75 mL of 0.5M K$_2$CO$_3$ and 2×75 mL of brine, dried (Na$_2$SO$_4$), and stripped of all solvent in vacuo. Following chromatography, 1.56 g of the title product as a white solid was obtained.

Calculated for C$_{25}$H$_{23}$N$_4$O$_3$Cl (MW=474.49): C, 63.36; H, 5.11; N, 11.81; Cl, 7.92. Found: C, 63.49; H, 5.00; N, 11.70; Cl, 8.23.

Example 56

1-[(8-chlorodibenz[b,f][1,4]oxazepin-10(11H)-yl)carbonyl]-4-(3-pyridinylacetyl)piperazine, monohydrochloride

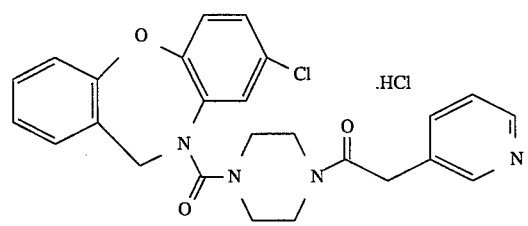

The title material was synthesized from the title material of Example 55 (1.26 g, 2.65 mmol) by the method of Example 5. A 1.32 g sample of the white solid title compound salt was obtained.

Calculated for C$_{25}$H$_{23}$N$_4$O$_3$Cl+HCl+0.75 H$_2$O (MW=512.91): C, 58.54; H, 5.01; N, 10.92; Cl, 13.82. Found: C, 58.56; H, 4.98; N, 10.65; Cl, 14.32.

Example 57

1-[(8-chlorodibenz[b,f][1,4]oxazepin-10(11H)-yl)carbonyl]-4-(3-pyridinylcarbonyl)piperazine

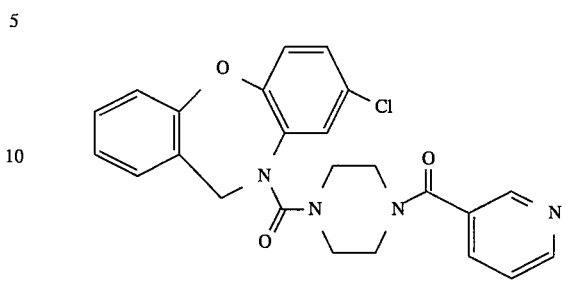

The title compound of Example 25 (0.5 g, 1.32 mmol) was coupled to 3-pyridine carboxylic acid (0.16 g, 1.32 mmol) by the procedure of Example 55. Following chromatographic separation of the crude product, 0.52 g of the title compound was obtained.

Example 58

1-[(8-chlorodibenz[b,f][1,4]oxazepin-10(11H)-yl)carbonyl]-4-(3-pyridinylcarbonyl)piperazine, hydrochloride

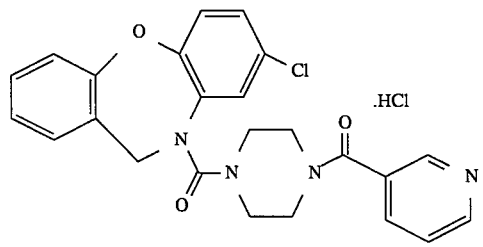

The title compound of Example 57 (0.45 g, 0.95 mmol) was converted to the title product by the method of Example 17. A 0.37 g sample of this material was obtained.

Calculated for C$_{24}$H$_{21}$N$_4$O$_3$Cl+0.3 HCl+0.3 H$_2$O (MW=465.25): C, 61.96; H, 4.74; N, 12.04; Cl, 9.91. Found: C, 61.66; H, 4.73; N, 11.87; Cl, 10.19.

Example 59 ethyl 4-[(8-chlorodibenz[b,f][1,4]oxazepin-10(11H)-yl)carbonyl]hexahydro-1H-1,4-diazepine-1-carboxylate

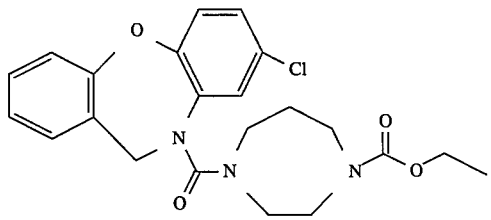

The title compound of Example 2 (2.0 g, 6.80 mmol) was reacted with the product of Example 96 (ethyl hexahydro-1H-1,4-diazacycloheptane-1-carboxylate) (1.29 g, 7.48 mmol) by the method of Example 4. Following chromatographic separation, 3.0 g of the yellow oil crude title product was obtained.

Calculated for C$_{22}$H$_{24}$N$_3$O$_4$Cl (MW=429.91): C, 61.47;

H, 5.63; N, 9.77; Cl, 8.25. Found: C, 61.28; H, 5.82; N, 9.55; Cl, 8.01.

Example 60

8-chloro-10-[(hexahydro-1H-1,4-diazepin-1-yl)carbonyl]-10,11-dihydrodibenz[b,f] [1,4]oxazepine

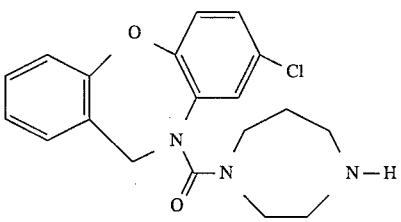

The title product of Example 59 (2.5 g, 5.8 mmol) was combined with 25 mL of concentrated HCl and 25 mL of dioxane. The solution was brought to reflux and maintained at reflux and under $N_2$ for 6 days. After cooling the reaction to room temperature, all solvent was removed in vacuo and the residue was dissolved in EtOAc. This solution was brought to pH 8 with 2N NaOH and the organic solution was dried, filtered, and stripped of all solvent under reduced pressure. The residue was purified by chromatography to give 1.0 g of the title compound.

Example 61

8-chloro-10-[(hexahydro-1H-1,4-diazepin-1-yl)carbonyl]-10,11-dihydrodibenz[b,f][1,4]oxazepine, hydrochloride

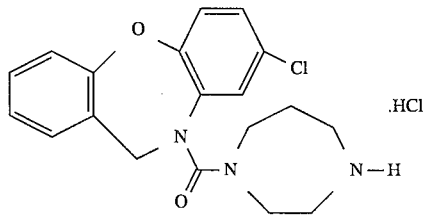

The title compound of Example 60 (0.20 g, 0.56 mmol) was converted to the title product by the method of Example 17. A 0.14 g sample of this material was obtained.
Calculated for $C_{19}H_{20}N_3O_2Cl+1.1$ HCl+0.2 $H_2O$ (MW= 401.55): C, 54.65; H, 5.19; N, 10.06; Cl, 17.83. Found: C, 54.41; H, 5.21; N, 9.85; Cl, 18.03.

Example 62

1,1-dimethylethyl 4-(2-furanylmethyl)-1-piperazinecarboxylate

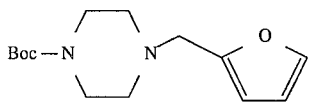

The title material was synthesized from t-butyloxycarbonyl piperazine (1.0 g, 5.4 mmol) and 2-furancarboxaldehyde (0.62 g, 6.5 mmol) by the method of Example 44. A 0.34 g sample of the crude title material was obtained and used without further purification.

Example 63

1-(2-furanylmethyl)piperazine hydrachloride

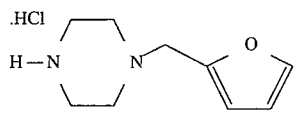

The title compound of Example 62 (0.34 g, 1.7 mmol) was converted to the title product by the method of Example 31. A 0.50 g sample of this material was obtained.

Example 64

8-chloro-10-[[4-(2-furanylmethyl)-1-piperazinyl]carbonyl]-10,11-dihydrodibenz[b,f] [1,4]oxazepine

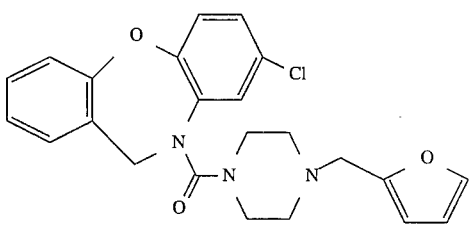

The title compound of Example 2 (0.91 g, 3.10 mmol) was reacted with the product of Example 63 (0.50 g, 3.10 mmol) by the method of Example 4 with the modification described in Example 32. Following chromatographic separation, 0.09 g of the solid title product was obtained.
Calculated for $C_{23}H_{22}N_3O_3Cl+0.5$ $H_2O+0.3$ $CH_2Cl_2$ (MW=458.34): C, 61.05; H, 5.19; N, 9.17; Cl, 12.37. Found: C, 60.71; H, 5.10; N, 9.16; Cl, 12.75.

Example 65

8-chloro-10-[[4-(2-furanylmethyl)-1-piperazinyl]carbonyl]-10,11-dihydrodibenz[b,f][1,4]oxazepine, monohydrochloride

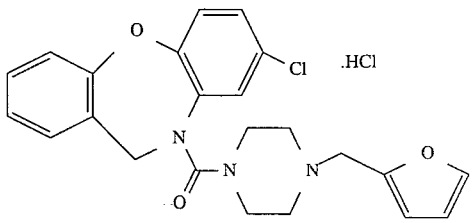

The title material was synthesized from the title material of Example 64 (0.09 g, 0.020 mmol) by the method of Example 5. A 0.056 g sample of the cream colored solid title compound salt was obtained.
Calculated for $C_{23}H_{22}N_3O_3Cl+HCl$ 0.5 $H_2O$ (MW=469.37): C, 58.86; H, 5.15; N, 8.95. Found: C, 58.53; H, 5.06; N, 8.86.

Example 66

COMPOUND A 8-chloro-10-[[4-[2-(diethylamino)ethyl]-3,6-dihydro-1(2H)-pyridinyl]carbonyl] -10,11-dihydrodibenz[b,f][1,4]oxazepine

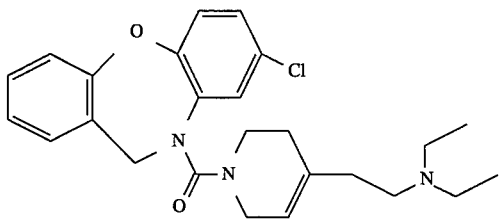

COMPOUND B 8-chloro-10-[[4-[2-(diethylamino)ethyl]-1-piperidinyl]carbonyl]-10,11-dihydrodibenz[b,f][1,4]oxazepine

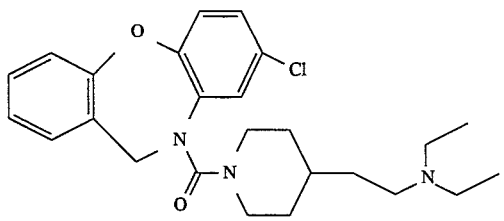

The title compound of Example 2 (1.5 g, 5.10 mmol) was reacted with a mixture of N,N-diethyl-1,2,3,6-tetrahydro-4-pyridinethanamine and N,N-diethyl-4-piperidineethanamine (0.95 g, 5.10 mmol) by the method of Example 4. Following chromatographic separation, 0.88 g of the solid COMPOUND A title product and 1.29 g of a mixture of title COMPOUNDS A and B were obtained.

COMPOUND A

Calculated for $C_{24}H_{30}N_3O_2Cl+0.03$ $CH_2Cl_2$ (MW=430.52): C, 67.04; H, 7.04 N, 9.76 Cl, 8.73. Found: C, 67.10; H, 6.90; N, 9.31; Cl, 8.80.

Example 67

8-chloro-10-[[4-[2-(diethylamino)ethyl]-3,6-dihydro-1(2H)-pyridinyl]carbonyl]-10,11-dihydeodibenz[b,f][1,4]oxazepine, hydrochloride

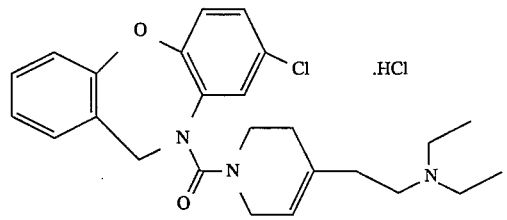

The title material was synthesized from of the title material of Example 66 (COMPOUND A) (0.09 g, 0.020 mmol) by the method of Example 5. A 0.056 g sample of the cream colored solid title compound salt was obtained.

Calculated for $C_{24}H_{30}N_3O_2Cl+0.125$ $H_2O+0.02$ $CH_2Cl_2$ (MW=430.92): C, 66,95; H, 6.85; N, 9.75 Cl, 8.58. Found: C, 67.10; H, 6.90; N, 9.31; Cl, 8.80.

Example 68

1-[[4-[(8-chlorodibenz[b,f][1,4]oxazepin-10(11H)-yl)carbonyl]-1-piperazinyl]acetyl]pyrrolidine

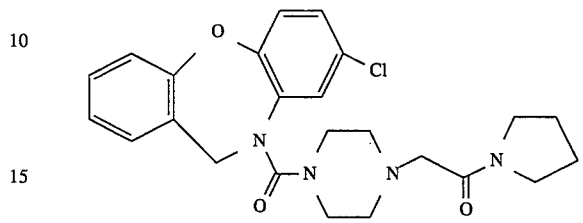

The title compound of Example 2 (0.75 g, 2.55 mmol) was reacted with 1-(1-piperazinylacetyl)pyrrolidine (0.50 g, 2.55 mmol) by the method of Example 4. Following chromatographic separation, 1.08 g of clear oil title product was obtained.

Example 69

1-[[4-[(8-chlorodibenz[b,f][1,4]oxazepin-10(11H)-yl)carbonyl]-1-piperazinyl]acetyl]pyrrolidine, hydrochloride

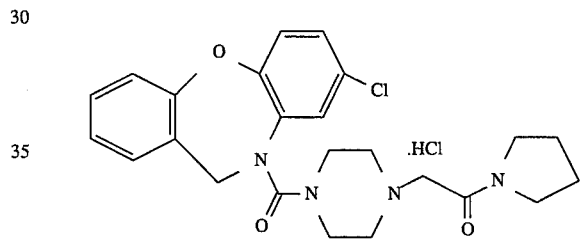

The title material was synthesized from the title material of Example 68 (0.95 g, 2.10 mmol) by the method of Example 5. A 0.84 g sample of the solid title compound salt was obtained.

Calculated for $C_{24}H_{27}N_4O_3Cl+1.4$ $HCl+1.5$ $H_2O$ (MW= 430.52): C, 54.08; H, 5.94; N, 10.51; Cl, 15.96. Found: C, 53.79; H, 5.64; N, 10.37; Cl, 15.99.

Example 70

8-chloro-10-[[4-(dimethylamino)-1-piperidinyl]carbonyl]-10,11-dihydrodibenz[b,f][1,4 oxazepine

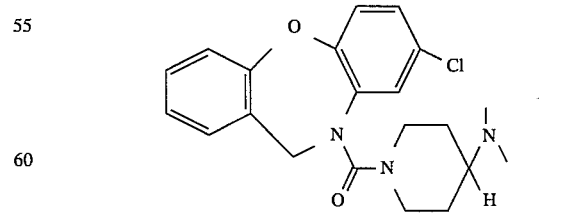

The title compound of Example 2 (1.0 g, 3.40 mmol) was reacted with N,N-dimethyl-4-piperidinamine (0.48 g, 3.74 mmol) by the method of Example 4. Following chromatographic separation, 0.32 g of the title product was obtained.

Example 71

8-chloro-10-[[4-(dimethylamino)-1-piperidinyl]carbonyl]-10,11-dihydrodibenz[b,f][1,4]oxazepine, monohydrochloride

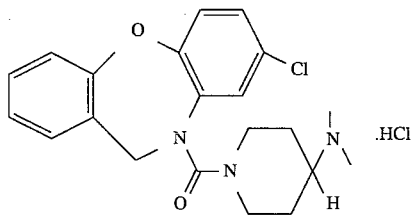

The title material was synthesized from the title product of Example 70 (0.30 g, 0.78 mmol) by the method of Example 5. A 0.84 g sample of the solid title compound salt was obtained.

Calculated for $C_{21}H_{24}N_3O_2Cl+1.1$ HCl+0.5 $H_2O$ (MW= 435.01): C, 58.12; H, 5.83; N, 9.68; Cl, 17.15. Found: C, 58.17; H, 5.65; N, 9.56; Cl, 17.03.

Example 72

1,1-dimethylethyl 4-(3-furanylmethyl)-1-piperazinecarboxylate

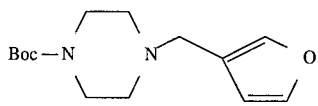

The title material was synthesized from t-butyloxycarbonyl piperazine (1.0 g, 5.4 mmol) and 3-furancarboxaldehyde (0.62 g, 6.4 mmol) by the method of Example 44. A 0.69 g sample of the crude title material was obtained and used without further purification.

Example 73

1-(3-furanylmethyl)piperazine hydrachloride

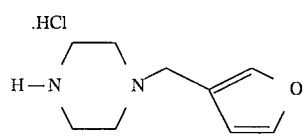

The title compound of Example 72 (0.69 g, 2.6 mmol) was converted to the title product by the method of Example 31. A 0.16 g sample of this material was obtained.

Example 74

8-chloro-10-[[4-(3-furanylmethyl)-1-piperazinyl]carbonyl]-10,11-dihydrodibenz[b,f] [1,4]oxazepine

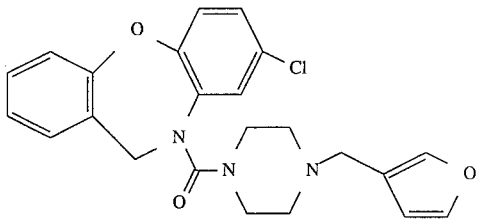

The title compound of Example 2 (0.29 g, 0.98 mmol) was reacted with the product of Example 73 (0.16 g, 0.98 mmol) by the method of Example 4 with the modification described in Example 32. Following chromatographic separation, 0.08 g of the solid title product was obtained.

Calculated for $C_{23}H_{22}N_3O_3Cl+0.25$ $H_2O+0.45$ $CH_2Cl_2$ (MW=466.62): C, 60.36; H, 5.05; N, 9.01; Cl, 14.44. Found: C, 60.05; H, 5.05; N, 8.93; Cl, 14.77.

Example 75

8-chloro-10-[[4-(3-furanylmethyl)-1-piperazinyl]carbonyl]-10,11-dihydrodibenz[b,f][1,4]oxazepine, monohydrochloride

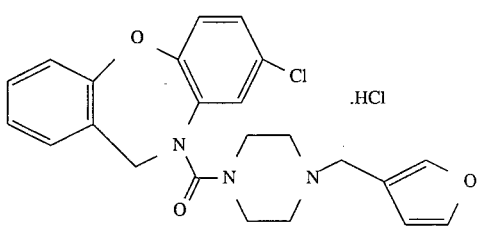

The title material was synthesized from the title material of Example 74 (0.06 g, 0.013 mmol) by the method of Example 5. A 0.023 g sample of the white solid title compound salt was obtained.

Calculated for $C_{23}H_{22}N_3O_3Cl+HCl$ 1.5 $H_2O$ (MW=487.38): C, 56.68; H, 5.38; N, 8.62; Cl, 14.55. Found: C, 56.55; H, 4.96; N, 8.51; Cl, 14.40.

Example 76

8-chloro-10,11-dihydro-10-[[4-(4-pyridinylmethyl)-1-piperazinyl]carbonyl]dibenz[b,f] [1,4]oxazepine

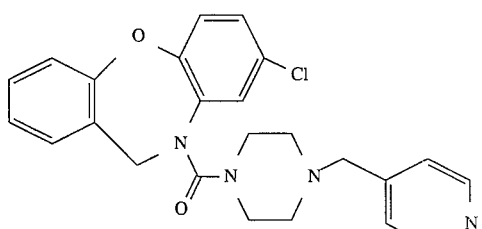

The title compound of Example 25 (1.5 g, 3.6 mmol) and 4-pyridine carboxaldehyde (excess) were reacted by the method of Example 39 to generate, after chromatographic purification, 87 mg of the title compound.

Calculated for $C_{24}H_{23}N_4O_2Cl+0.01$ $CH_2Cl_2+1.0$ $H_2O$ (MW=453.79): C, 63.55; H, 5.56; N, 12.35; Cl, 7.97. Found: C, 63.41; H, 5.54; N, 12.99; Cl, 7.99.

Example 77

8-chloro-10,11-dihydro-10-[[4-(4-pyridinylmethyl)-1-piperazinyl]carbonyl]dibenz[b,f][1,4]oxazepine, monohydrochloride

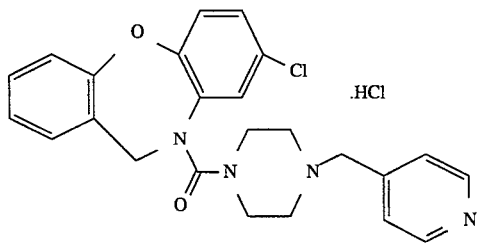

The title material was synthesized from the title product of Example 76 (0.05 g, 0.11 mmol) by the method of Example 5. A 0.025 g sample of the solid title compound salt was obtained.

Calculated for $C_{24}H_{23}N_4O_2Cl+1.0$ HCl+0.5 $H_2O$ (MW=480.40): C, 60.01; H, 5.25; N, 11.66; Cl, 14.76. Found: C, 59.77; H, 5.33; N, 11.63; Cl, 14.77.

Example 78

1-[(8-chlorodibenz[b,f][1,4]oxazepin-10(11H)-yl)carbonyl]-4-(4-pyridinylacetyl)piperazine

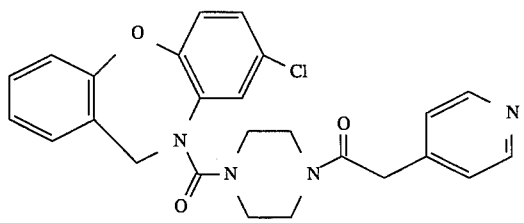

The title compound of Example 25 (1.38 g, 3.64 mmol) was coupled to 4-pyridyl acetic acid (0.63 g, 3.64 mmol) by the procedure of Example 55. Following chromatographic separation of the crude product, 0.91 g of the title compound was obtained as a white solid.

Example 79

1-[(8-Chlorodibenz[b,f][1,4]oxozepin-10(11H)-yl)carbonyl]-4-[1-oxo-2-(4-pyridinyl)ethyl]piperazine, monohydrochloride, monohydrate

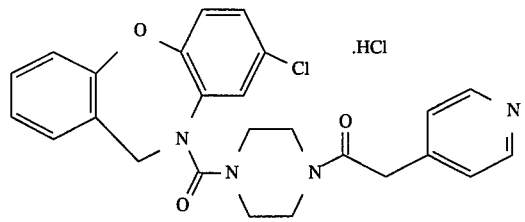

The title compound was synthesized from the title product of Example 78 (0.50 g, 1.08 mmol) by the method of Example 17. A 0.50 g sample of the white fluffy solid title product was obtained.

Calculated for $C_{25}H_{23}N_4O_3Cl+1.0$ HCl+1.0 $H_2O$ (MW=517.42): C, 58.03; H, 5.07; N, 10.83; Cl, 13.70. Found: C, 58.28; H, 4.93; N, 10.80; Cl, 13.44.

Example 80

1-[(8-chlorodibenz[b,f][1,4]oxazepin-10(11H)-yl)carbonyl] hexahydro-4-(4-pyridinylacetyl)-1H-1,4-diazepine

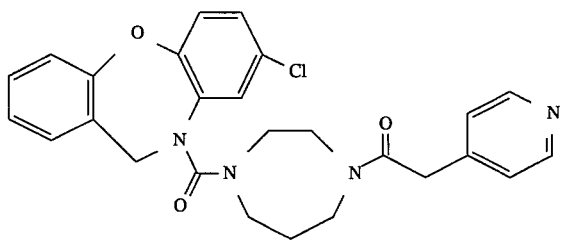

The title compound of Example 61 (1.43 g, 3.64 mmol) was coupled to 4-pyridyl acetic acid (0.63 g, 3.64 mmol) by the procedure of Example 55. Following chromatographic separation of the crude product, 0.56 g of the title compound was obtained as a white solid.

Example 81

1-[(8-chlorodibenz[b,f][1,4]oxazepin-10(11H)-yl)carbonyl] hexahydro-4-(4-pyridinylacetyl)-1H-1,4-diazepine, monohydrochloride

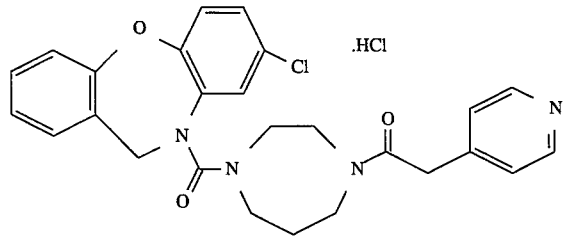

The title compound was synthesized from the title product of Example 80 (0.50 g, 1.08 mmol) by the method of Example 17. A 0.50 g sample of the white fluffy solid title product was obtained.

Calculated for $C_{26}H_{25}N_4O_3Cl+1.0\ HCl+0.25\ H_2O$ (MW= 517.93): C, 60.30; H, 5.16; N, 10.82; Cl, 13.69. Found: C, 60.32; H, 5.45; N, 10.90; Cl, 13.20.

Example 82

1-[(8-chlorodibenz[b,f][1,4]oxazepin-10(11H)-yl)carbonyl]-4-[[5-(2-pyridinyl)-2-thienyl]carbonyl]piperazine

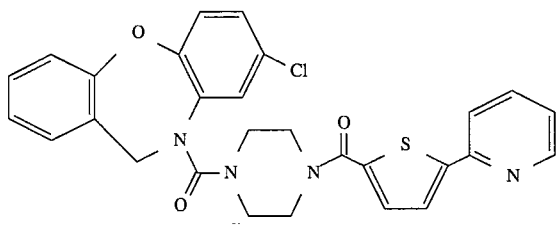

The title compound of Example 25 (1.5 g, 3.85 mmol) was coupled to 5-(pyrid-2-yl)thiophene-2-carboxylic acid (1.5 g, 3.85 mmol) by the procedure of Example 55. Following chromatographic separation of the crude product, 0.84 g of the title compound was obtained as a white solid.

Calculated for $C_{28}H_{23}N_4O_3SCl+0.75\ H_2O$ (MW=544.55): C, 61.76; H, 4.54; N, 10.29; S, 5.89; Cl, 6.51. Found: C, 61.89; H, 4.22; N, 10.12; S, 5.91; Cl, 5.91.

Example 83

1-[(8-chlorodibenz[b,f][1,4]oxazepin-10(11H)-yl)carbonyl]-4-[[5-(2-pyridinyl)-2-thienyl]carbonyl]piperazine hydrochloride

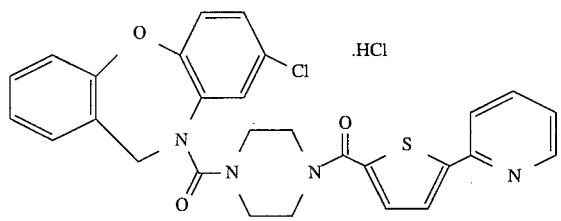

The title material was synthesized from the title material of Example 82 (0.74 g, 1.36 mmol) by the method of Example 5. A 0.50 g sample of the white solid title compound salt was obtained.

Calculated for $C_{28}H_{23}N_4O_3SCl+HCl+H_2O$ (MW=585.51): C, 57.44; H, 4.63; N, 9.57; S; 5.48; Cl, 12.11. Found: C, 57.71; H, 4.36; N, 9.69; S, 5.64; Cl, 12.52.

Example 84

Ethyl 2-thiophenepropionate

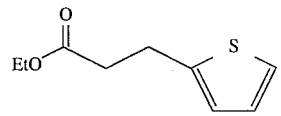

Ethylacrylate (10.0 g, 100 mmol), 2-bromothiophene (16.3 g, 100 mmol), palladium(II) acetate (0.5 g, 2.22 mmol), and tri-o-tolylphosphine (1.62 g, 5.4 mmol) were dissolved in a mixture of triethylamine (40 mL) and acetonitrile (140 mL). This solution was refluxed under nitrogen ($N_2$) for 17 hours before it was diluted with EtOAc (250 mL) and $H_2O$ (115 mL). This mixture was filtered through celite and the aqueous layer discarded. The organic layer was washed with 1×75 mL of $H_2O$ and 2×75 mL of brine, dried over $Na_2SO_4$ and stripped of all solvent under reduced pressure to provide 22.3 g of crude product, The unsaturated 2-thiophenyl ethyl ester material, 13.9 g as a pale yellow liquid, was obtained after chromatographic purification.

A 7.0 g sample of this material was reduced to the title product in a Standard Parr hydrgenation apparatus using 10% Pd on carbon as catalyst and ethanol as solvent. The reaction was run at room temperature for 23 hours under a hydrogen pressure of 5 psi. The reaction mixture was then filtered and all solvent was removed under reduced pressure to yield 2.9 g of the crude title product. This material was used in Example 85 without further purification.

Example 85

1-[(8-chlorodibenz[b,f][1,4]oxazepin-10(11H)-yl)carbonyl]-4-[1-oxo-3-(2-thienyl)propyl]piperazine

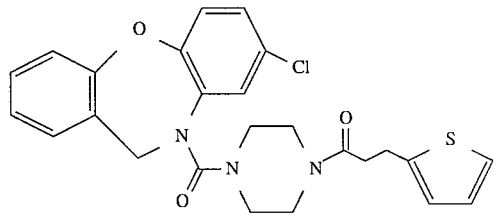

The title product of Example 25 (1.0 g, 2.57 mmol) and triethyl amine (0.26 g, 2.57 mmol) were dissolved in 30 mL of methylene chloride. To this solution was added trimethyl aluminum (2.0M in hexane, 1.6 mL, 3.08 mmol) and the product of Example 84 (0.57 g, 2.72 mmol). This mixture was refluxed under $N_2$ for 3 days before it was cooled to room temperature and partitioned between EtOAc (300 mL) and 0.5N $KHSO_4$ (75 mL). The aqueous layer was discarded and the organic layer was washed with 100 mL of brine, dried over $Na_2SO_4$ and stripped of all solvent under reduced pressure to provide the crude product. The title product (0.45 g) was obtained as a white solid following chromatographic purification.

Calculated for $C_{25}H_{24}N_3O_3SCl+0.125\ H_2O+0.01\ CH_2Cl_2$ (MW=485.10): C, 61.92; H, 5.04; N, 8.66; S; 6.61; Cl, 7.45. Found: C, 61.91; H, 5.15; N, 8.60; S, 6.64; Cl, 7.73.

Example 86

1-[(8-chlorodibenz[b,f][1,4]oxazepin-10(11H)-yl)carbonyl]hexahydro-4-[1-oxo-3-(3-pyridinyl)propyl]-1H-1,4-diazepine

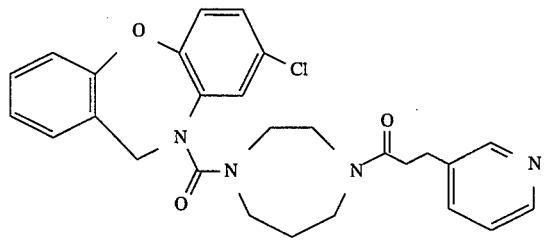

The title compound of Example 60 (0.73 g, 2.0 mmol) was coupled to 3-(3-pyridyl)propanoic acid (0.31 g, 2.0 mmol) by the procedure of Example 55. Following chromatographic separation of the crude product, 0.60 g of the title compound was obtained as a white solid and used in Example 87 without further purification.

Example 87

1-[(8-chlorodibenz[b,f][1,4]oxazepin-10(11H)-yl)carbonyl]hexahydro-4-[1-oxo-3-(3-pyridinyl)propyl]-1H-1,4-diazepine, monohydrochloride

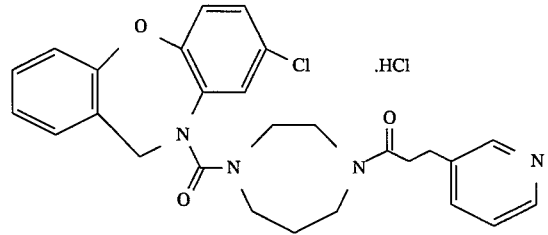

The title compound was synthesized from the title product of Example 86 (0.25 g, 0.51 mmol) by the method of Example 17. A 0.25 g sample of the slightly off white fluffy solid title product was obtained.

Calculated for $C_{27}H_{27}N_4O_3Cl+1.0\ HCl+0.40\ H_2O$ (MW= 534.66): C, 60.66; H, 5.43; N, 10.48; Cl, 13.26. Found: C, 60.69; H, 5.53; N, 10.47; Cl, 12.88.

Example 88

1-[2-(4-pyridinyl)ethyl]piperazine

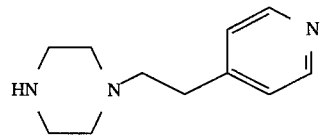

To a melt of piperazine (15 g, 0.17 mol) heated to 105° C. was added dropwise 4-vinylpyridine (1.25 mL, 0.012 mol). After refluxing the reaction for 5.5 hours, it was cooled to room temperature and chromatographed to provide 0.92 g of the title compound.

Example 89

8-chloro-10,11-dihydro-10-[[4-[2-(4-pyridinyl)ethyl]-1-piperazinyl]carbonyl]dibenz[b,f][1,4]oxazepine

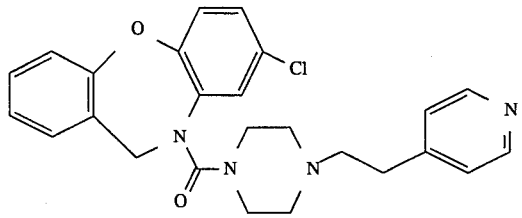

The title compound of Example 2 (0.38 g, 1.3 mmol) was combined with the product of Example 88 (0.25 g, 1.3 mmol) and the reaction was carried out by the method of Example 4. Following chromatographic separation, 1.7 g of the white solid title product was obtained.

Example 90

8-chloro-10,11-dihydro-10-[[4-[2-(4-pyridinyl)ethyl]-1-piperazinyl]carbonyl]dibenz[b,f][1,4]oxazepine, monohydrochloride

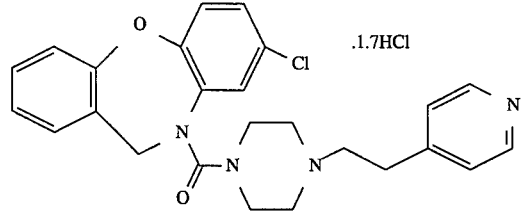

The title compound was synthesized from the title product of Example 89 (0.36 g, 0.80 mmol) by the method of Example 17. A 0.38 g sample of the white fluffy solid title product was obtained.

Calculated for $C_{25}H_{25}N_4O_2Cl+1.7\ HCl+0.7\ H_2O$ (MW= 523.55): C, 57.35; H, 5.41; N, 10.70; Cl, 18.28. Found: C, 57.49; H, 5.43; N, 10.39; Cl, 18.01.

Example 91

1-[(8-chlorodibenz[b,f][1,4]oxazepin-10(11H)-yl)carbonyl]
-4-[(6 -quinolinyl)carbonyl]piperazine

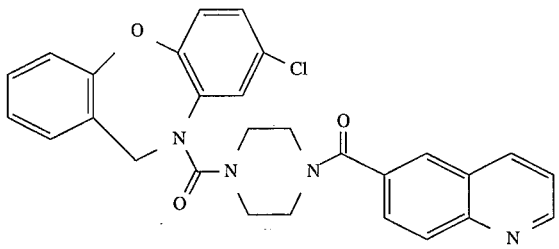

The title compound of Example 25 (1.5 g, 3.85 mmol) was coupled to 6-quinolinecarboxylic acid (0.67 g, 3.85 mmol) by the procedure of Example 55. Following chromatographic separation of the crude product, 1.23 g of the title compound was obtained as a white solid.

Calculated for $C_{28}H_{23}N_4O_3Cl+0.1$ $CH_2Cl_2+0.15$ EtOAc (MW=520.52): C, 65.88; H, 4.67; N, 10.76; Cl, 8.85. Found: C, 65.64; H, 4.65; N, 10.86; Cl, 8.81.

Example 92

1-[(8-chlorodibenz[b,f][1,4]oxazepin-10(11H)-yl)carbonyl]
hexahydro-4-[(6 -quinolinyl)carbonyl]-1H-1,4-diazepine

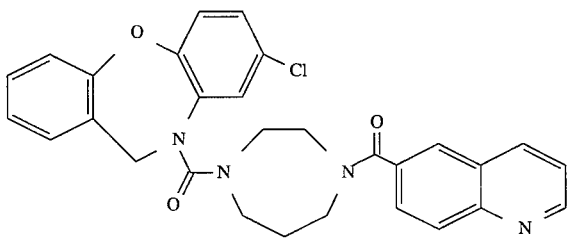

The title compound of Example 61 (1.58 g, 4.0 mmol) was coupled to 6-quinolinecarboxylic acid (0.69 g, 4.0 mmol) by the procedure of Example 55. Following chromatographic separation of the crude product, 1.35 g of the title compound was obtained as a white solid.

Calculated for $C_{29}H_{25}N_4O_3Cl+0.2$ $H_2O$ (MW=516.60): C, 67.43; H, 4.96; N, 10.85; Cl, 6.86. Found: C, 67.31; H, 4.90; N, 10.73; Cl, 6.97.

Example 93

1-[(8-chlorodibenz[b,f][1,4]oxazepin-10(11H)-yl)carbonyl]
hexahydro-4-[(6 -quinolinyl)carbonyl]-1H-1,4-diazepine, monohydrochloride

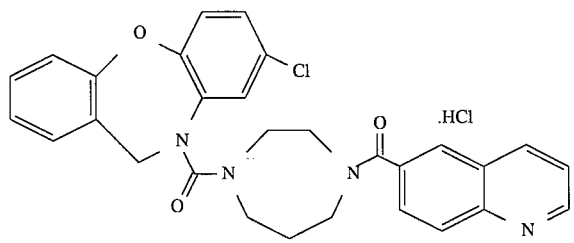

The title compound was synthesized from the title material of Example 92 (0.50 g, 0.97 mmol) by the method of Example 17. A 0.42 g sample of the white fluffy solid title product was obtained.

Calculated for $C_{25}H_{25}N_4O_2Cl+1.7$ HCl+0.7 $H_2O$ (MW= 523.55): C, 57.35; H, 5.41; N, 10.70; Cl, 18.28. Found: C, 57.49; H, 5.43; N, 10.39; Cl, 18.01.

Example 94

Ethyl 4-pyridinepropanoate

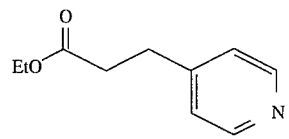

Ethylacrylate (10.0 g, 100 mmol), 4-bromopyridine (19.4 g, 100 mmol), palladium(II) acetate (0.5 g, 2.22 mmol), and tri-o-tolylphosphine (1.62 g, 5.4 mmol) in a mixture of triethylamine (40 mL) and acetonitrile (140 mL) were reacted as described in Example 84. The unsaturated 4-pyridyl ethyl ester product, 15.0 g as a clear liquid, was obtained after chromatographic purification.

A 7.5 g (42.3 mmol) sample of this material was reduced to the title product in a Standard Parr hydrgenation apparatus using raney nickel as catalyst and ethanol as solvent. The reaction was run at room temperature for 23 hours under a hydrogen pressure of 5 psi. The reaction mixture was then filtered and all solvent was removed under reduced pressure to yield 7.02 g of the crude title product. This material was used in the following reaction without further purification.

Example 95

1-[(8-chlorodibenz[b,f][1,4]oxazepin-10(11H)-yl)carbonyl]
-4-[1-oxo-3-(4-pyridinyl)-propyl]piperazine

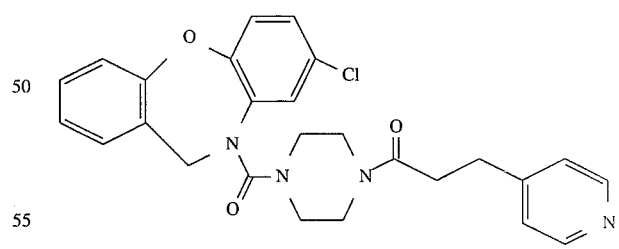

The product of Example 94 (0.46 g, 2.57 mmol) and the product of Example 25 (1.0 g, 2.57 mmol) were reacted as described in Example 85. Following silica gel chromatropraphy, 0.39 g of the title compound was isolated as a white powder.

Calculated for $C_{26}H_{25}N_4O_3Cl+0.05$ $CH_2Cl_2+0.125$ $H_2O$ (MW=483.46): C, 64.72; H, 5.29; N, 11.59 Cl, 8.07. Found: C, 64.83; H, 5.30; N, 11.60; Cl, 8.11.

Example 96

Ethyl hexahydro-1H-1,4-diazepine-1-carboxylate

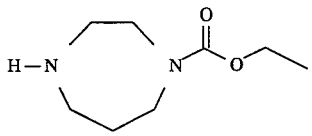

To a solution of homopiperazine (50.0 g, 0.5 mol) in aqueous HCl adjusted to pH 4 using approximately 400 mL of 2N HCl was added ethyl chloroformate (50 mL, 0.53 mol) dropwise maintaining the pH at 4 by the addition of 25% aqueous NaOH. The reaction mixture was brought to pH 14 with 25% aqueous NaOH and extracted with 3×250 mL of Et₂O. These extracts were discarded and the aqueous was brought to pH 10 with 2N HCl and Na₂CO₃. After extracting the aqueous with 3×150 mL of Et₂O, these combined extracts were dried over Na₂SO₄, and stripped of all solvent under reduced pressure. The residue was vacuum distilled at 0.1 mm of Hg and the title compound was obtained as the fraction (25.0 g) distilling at 103° C.

Example 97

Ethyl hexahydro-4-(2-phenylethyl)-1H-1,4-diazepine-1-carboxylate

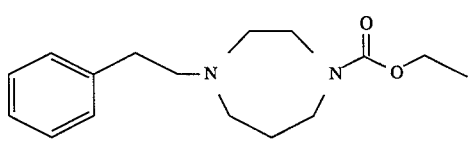

The product of Example 96 (0.75 g, 4.35 mmol) and phenylacetaldehyde (0.59 g, 4.91 mmol) were reacted as described in Example 39. The title product (1.07 g) was obtain as a light yellow liquid after work up and was used in Example 98 without further purification.

Example 98

Hexahydro-1-(2-phenylethyl)-1H-1,4-diazepine

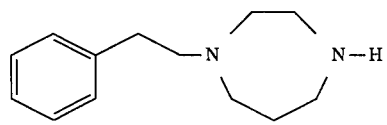

The title material of Example 97 (0.80 g, 2.90 mmol) was dissolved in 20 mL of concentrated HCl and heated to reflux for 18 hours. After cooling the reaction to room temperature, it was diluted with 15 mL of water and made basic with 2N NaOH. This mixture was extracted with EtOAc and this EtOAc solution was dried over Na₂SO₄ and stripped of all solvent under reduced pressure to provide 0.53 g of the title material as a yellow oil. This product was used in subsequent reactions without further purification.

Example 99

8-chloro-10,11-dihydro-10-[[hexahydro-4-(2-phenylethyl)-1H-1,4-diazepin-1-yl]carbonyl]dibenz[b,f][1,4]oxazepine

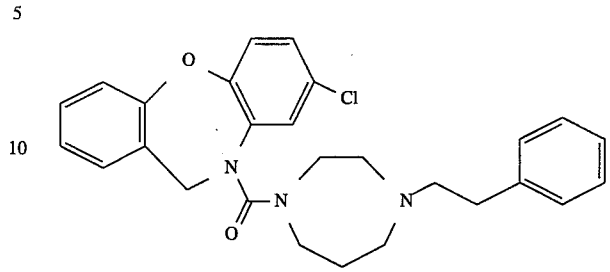

The title compound of Example 2 (0.72 g, 2.45 mmol) was combined with the title material of Example 98 (0.50 g, 2.45 mmol) and the reaction was carried out by the method of Example 4. Following chromatographic separation, 0.63 g of the white solid title product was obtained.

Example 100

8-chloro-10,11-dihydro-10-[[hexahydro-4-(2-phenylethyl)-1H-1,4-diazepin-1-yl]carbonyl]dibenz[b,f][1,4]oxazepine, monohydrochloride

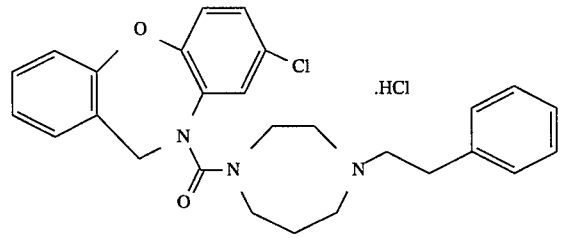

The title compound was synthesized from the title material of Example 99 (0.62 g, 1.35 mmol) by the method of Example 17. A 0.05 g sample of the white fluffy solid title product was obtained.
Calculated for $C_{27}H_{28}N_3O_2Cl+1.5$ HCl+2.0 $H_2O$ (MW= 552.72): C, 58.67; H, 6.11; N, 7.60; Cl, 16.04. Found: C, 58.79; H, 5.68; N, 7.56; Cl, 15.90.

Example 101

8-chloro-10,11-dihydro-10-[[4-[2-[(phenylmethyl)amino]ethyl]-1-piperazinyl]carbonyl]dibenz[b,f][1,4]oxazepine

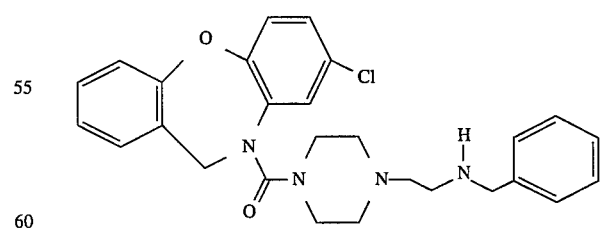

The title compound of Example 2 (0.72 g, 2.45 mmol) was combined with N-(phenylmethyl)-1-piperazineethanamine (0.75 g, 3.40 mmol) and the reaction was carried out by the method of Example 4. Following chromatographic separation, 0.52 g of the white solid title product was obtained.

Example 102

8-chloro-10,11-dihydro-10-[[4-[2-[(phenylmethyl)amino]ethyl]-1-piperazinyl]carbonyl]dibenz[b,f][1,4]oxazepine, monohydrochloride

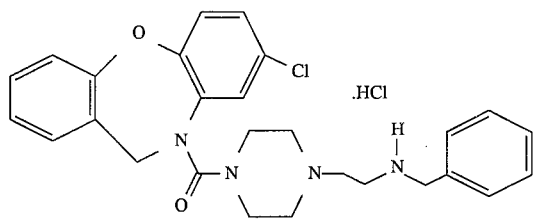

The title compound was synthesized from the title material of Example 101 (0.37 g, 0.81 mmol) by the method of Example 17. A 0.05 g sample of the white fluffy solid title product was obtained.

Calculated for $C_{26}H_{28}N_5O_2Cl+2.9$ HCl+1.5 $H_2O$ (MW= 610.76): C, 51.13; H, 5.59; N, 11.47; Cl, 22.64. Found: C, 51.23; H, 5.54; N, 11.29; Cl, 22.61.

Example 103

8-chloro-10-[[4-[2-(diethylamino)ethyl]piperidinyl]carbonyl]-10,11-dihydrodibenz[b,f] [1,4]oxazepine

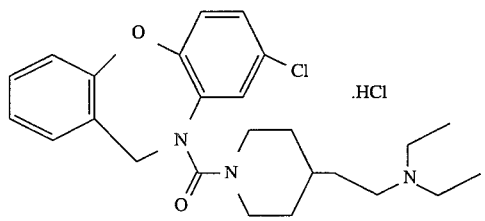

The title material is synthesized from COMPOUND B of the title material of Example 66 by the method of Example 5.

Example 104

8-chloro-10,11-dihydrodibenz[b,f][1,4]thiazepine

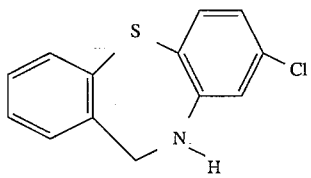

(a) 4-chloro-2-nitro-1-(phenylthio)benzene

Potassium hydroxide (6.15 g; 87%) was added to a stirred solution of thiophenol (10.0 g) in N,N-dimethylformamide (170 mL) at room temperature. When most of the potassium hydroxide appeared to have dissolved, 2,5-dichloronitrobenzene (17.4 g) was added, and the initially dark solution turned bright yellow with some precipitate. The reaction was placed in an oil bath at 70° C. for three hours, and then evaporated in vacuo. The residue was partitioned between chloroform and 1N NaOH and the layers were separated. The aqueous layer was extracted once more with chloroform. The chloroform solutions were combined, washed with 1N NaOH, $H_2O$, 1N HCl, $H_2O$ and brine, dried over $MgS_4$, and evaporated in vacuo. The resulting oil was treated with cyclohexane, and the product crystallized. The crystalline product was collected by filtration, washed with hexane, and dried in vacuo at 56° C. to yield 13.73 g (57%) of yellow crystals. mp: 84°–86° C.

(b) 5-chloro-2(phenylthio)benzenamine

A solution of 4-chloro-2-nitro-1-(phenylthio)benzene (11.0 g) and Raney nickel in ethanol (3A; 9.3 mL) was reacted in a Parr Hydrogenator under hydrogen atmosphere at 5 psi and room temperature. When the theoretical amount of hydrogen uptake was reached, the reaction was filtered to remove the catalyst and evaporated in vacuo to yield 8.61 g (88%) of a light orange solid. mp: 59°–61° C.

(c) 8-chloro-10,11-dihydrodibenzo[b,f][1,4]thiazepine

To a cold (ice water bath), stirred solution of phosgene (1.93M in toluene; 55 mL) under a nitrogen atmosphere was added, dropwise, a solution of 5-chloro-2-(phenylthio)benzenamine (5.00 g) in toluene (20 mL). The reaction mixture was stirred for 30 minutes in the ice bath, and was then heated on a steam bath for 30 minutes. The resulting orange solution was evaporated in vacuo to an oil (IR: weak band at approximately 2250 cm$^{-1}$).

The oil was taken up in bromobenzene (25 mL) and added dropwise to a stirred mixture of aluminum chloride (2.90 g) in bromobenzene (25 mL) in an oil bath at 100° C. When the addition was complete, the oil bath temperature was increased to 150° C., and the reaction was stirred for 1.5 hours. A small amount of water was then added to quench the reaction, and the mixture was evaporated in vacuo. The residue was triturated with acetone, and the solid was collected by filtration, washed with acetone followed by ether, and dried in vacuo at 110° C. for 16 hours to yield 6.99 g of white solid.

The white solid (6.64 g) was suspended with stirring in anhydrous tetrahydrofuran (175 mL) under a nitrogen atmosphere in an ice-$H_2O$ bath, and lithium aluminum hydride (1.0M in THF; 100 mL) was added dropwise, keeping the temperature below 10° C. When the addition was complete, the ice bath was removed and the reaction was stirred to room temperature (approximately 20 minutes), and then at reflux for four hours under a nitrogen atmosphere. The reaction was then cooled in an ice-$H_2O$ bath and quenched by the successive addition of $H_2O$ (3.8 mL), 15% NaOH (3.8 mL), and $H_2O$ (11.4 mL) while keeping the temperature below 15° C. The resulting mixture was filtered through filter aide and the filter cake was washed with THF. The filtrate and washes were combined and evaporated in vacuo to a yellow oil. The oil was flash chromatographed through silica gel 60 (approximately 300 mL) using chloroform. The collected product was recrystallized from cyclohexane to yield 2.37 g (42.7%) of product as white plates. mp: 125°–127° C.

Example 105

8-chlorodibenz[b,f][1,4]thiazepine-10(11H)-carbonyl chloride

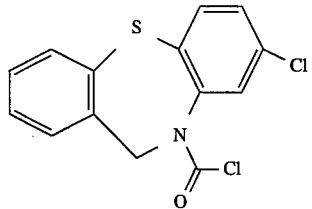

To a cold (ice-H₂O bath), stirred solution of phosgene (1.93M in toluene; 8.6 mL) in anhydrous tetrahydrofuran (40 mL) under a nitrogen atmosphere is added, dropwise, a solution of the product of Example 104 (8-chloro-10,11-dihydrodibenzo[b,f][1,4]thiazepine) (2.00 g) and triethylamine (1.3 mL) in anhydrous tetrahydrofuran (30 mL). The resulting mixture is stirred at room temperature for 90 minutes, and the solvent is then evaporated in vacuo to provide the title product.

Example 106

1-[(8-chlorodibenz[b,f][1,4]thiazepin-10(11H)-yl)carbonyl]-4-(2-furanylmethyl)piperazine

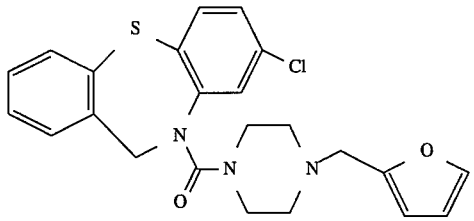

The title compound of Example 105 is reacted with the product of Example 63 by the method of Example 4. Following chromatographic separation, the title product is obtained.

Example 107

1-[(8-chlorodibenz[b,f][1,4]thiazepin-10(11H)-yl)carbonyl]-4-(2-furanylmethyl)piperazine monohydrochloride

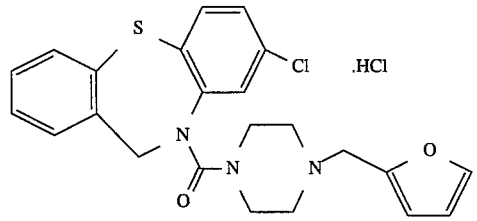

The title material is synthesized from the title material of Example 106 by the method of Example 5.

Example 108

1-[(8-chlorodibenz[b,f][1,4]thiazepin-10(11H)-yl)carbonyl]-4-(2-furanylmethyl)piperazine S-oxide monohydrochloride

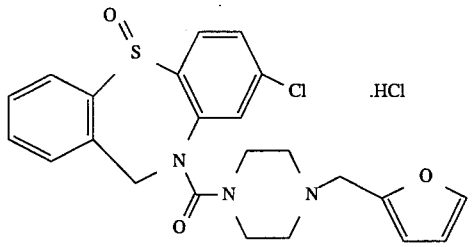

The title material is synthesized from the title material of Example 107 by treatment of this compound with 30% H₂O₂ in acetic acid at room temperature.

Example 109

1-[(8-chlorodibenz[b,f][1,4]thiazepin-10(11H)-yl-carbonyl]-4-(2-furanylmethyl)piperazine S,S-dioxide monohydrochloride

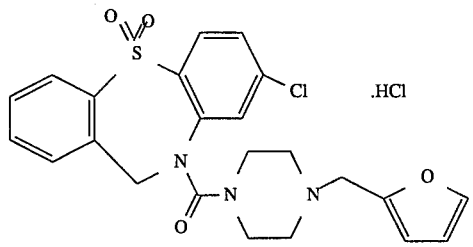

The title material is synthesized from the title material of Example 107 by treatment of this compound with 30% H₂O₂ in acetic acid at 50° C.

Example 110

8-chloro-10(11H)-[1-(phenylmethyl)-4-piperidinylmethyl]dibenz[b,f][1,4] thiazepine

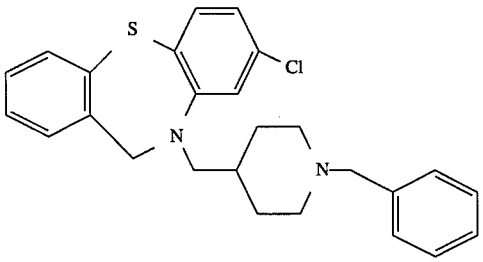

A sample of 1-benzylpiperidine-4-carboxylic acid ethyl ester is reduced to 1-benzylpiperidine-4-hydroxymethyl by treatment with lithium aluminum hydride (LiAlH₄) in THF. This material is converted to its methane sulfonate by reaction with methanesulfonyl chloride. This material, 1-benzylpiperidine-4-methyl-methane sulfonate, the product of Example 104, and diisopropylethyl amine are refluxed in toluene the provide the title compound.

Example 111

8-chloro-10(11H)-[1-(phenylmethyl)-4-piperidinylmethyl]dibenz[b,f][1,4]-thiazepine monohydrochloride

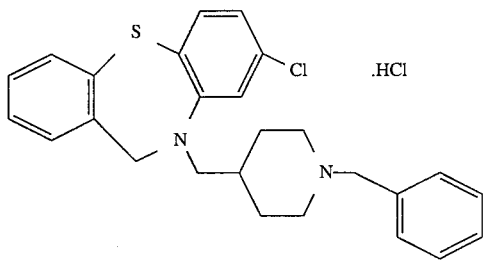

The title material is synthesized from the title material of Example 110 by the method of Example 5.

Example 112

8-chloro-10(11H)-[[1-(phenylmethyl)-4-piperidinyl]carbonyl]dibenz[b,f][1,4]oxazepine

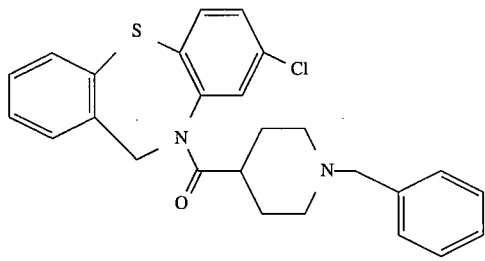

A sample of 1-benzylpiperidine-4-carboxylic acid ethyl ester is reacted in refluxing methylene chloride with the product of Example 104 and trimethyl aluminum to yield the title product.

Example 113

8-chloro-10(11H)-[[1-(phenylmethyl)-4-piperidinyl]carbonyl]dibenz[b,f][1,4]oxazepine hydrochloride

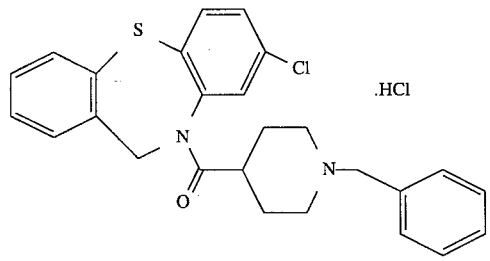

The title material is synthesized from the title material of Example 112 by the method of Example 5.

The foregoing examples are provided to enable one of ordinary skill in the art to practice the present invention. These examples are merely illustrative, however, and should not be read as limiting the scope of the invention as it is claimed in the appended claims.

Biological Assays (a) The Writhing Assay

The Writhing Assay is one of the most widely-used experimental procedures for measuring the analgesic activity of different narcotic and nonnarcotic analgesic agents, and involves the continuous, chemically-induced pain of visceral origin to an animal, such as a mouse or rat. [Gyires et al., *Arch. int. Pharmacodyn*, 267, 131–140 (1984); C. Vander Wende et al., *Fed. Proc.*, 15, 494 (1956); Koster et al., *Fed. Proc.*, 18, 412 (1959); and Witken et al., *J. Pharmacol. exp. Ther.*, 133, 400–408 (1961).] Chemicals which may be used to induce this pain include phenylbenzoquinone (PBQ) and acetic acid. As a result of the chemical irritation to the animal, a characteristic stretching and writhing of the animal (dorsiflexion of the animal's back, extension of its hindlimbs and the strong contraction of its abdominal musculature) will generally occur. The intensity of this pain reaction is determined by the number of writhes exhibited by the animal during a given period of time. Drugs which reduce the number of writhes of the animal appear to restore the normal nociceptive threshold of the animal.

Compounds of the present invention exhibit analgesic activity in mice, as shown by the results of the Writhing Assay presented in Table 1 below.

Charles River male albino mice, weighing 20 to 30 grams were used in this assay.

Twenty-five minutes after intragastric administration to nine or ten mice of 30 mg per kilogram of body weight of a compound of the present invention ("test compound"), 0.1 mg per 10 g of body weight of a 0.025% w/v solution of PBQ was injected intraperitoneally into each mouse. Ten mice which were given saline in place of a test compound of the invention were used as a control group.

Five minutes later, each mouse was individually placed into a glass beaker for observation, and the number of writhes occurring during the following ten-minute period was counted.

A test compound was considered to have produced analgesia in a mouse if, in accordance with the conditions set forth above, and under the test criteria employed for this assay, after the administration of 30 mg per kilogram of body weight of a compound of the present invention to the mouse, the number of writhes elicited by a mouse injected with PBQ was equal to, or less than, one-half the median number of writhes recorded for the saline-treated control group of mice that day, as described by Taber in "Predictive Value of Analgesic Assays in Mice and Rats," *Advances in Biochemical Psychopharmacology*, 8, 191 (1974).

The standard initial screening dose of a test compound employed in this assay was 10 mpk per gram of body weight. If this initial screening dose of the test compound produced analgesia in seven of nine or ten mice, then the effect of additional doses of the test compound on the writhing response was evaluated, and then the $ED_{50}$ value (that dose of a compound which produced analgesia in 50% of the mice to which the compound was administered) was generally calculated. A maximum likelihood function was used to determine the $ED_{50}$ value. (The slopes of the dose-response curves for all test compounds analyzed were compared as described by Tallarida and Murray, *Manual of Pharmacologic Calculations*, Page 11 (Springer Verlag, New York, 1981).

The results for the particular compounds of the present invention analyzed in this assay, and discussed in the examples identified below which correspond thereto, are presented in Table 1 hereinbelow. The compounds of the present invention which were tested in this assay, and for which results are presented in Table 1, correspond to the particular examples specified in Table 1. The fractions indicate the number of mice out of nine or ten in which a test compound produced analgesia, and the whole numbers are the calculated $ED_{50}$ values.

TABLE 1

Data Generated from the Writhing Assay

| Compound Tested | Intragastric |
|---|---|
| Example 3 | 2/10 |
| Example 5 | 4/10 |
| Example 7 | 6.8 |
| Example 9 | 9.7 |
| Example 11 | 1/10 |
| Example 13 | 9/10 |
| Example 15 | 6.4 |
| Example 17 | 5.1 |
| Example 19 | 2/9 |
| Example 20 | 4/10 |
| Example 22 | 3/10 |
| Exmaple 24 | 14.7 |
| Example 25 | 5/10 |
| Example 29 | 5/10 |
| Example 33 | 8/10 |
| Example 34 | 7/10 |
| Example 38 | 1/10 |
| Example 40 | 2/10 |
| Example 41 | 10/10 |
| Example 43 | 1/10 |
| Example 47 | 7/10 |
| Example 49 | 2/10 |
| Example 54 | 6/10 |
| Example 56 | 5/10 |
| Example 58 | 7/10 |
| Example 61 | 6/10 |
| Example 65 | 4/10 |
| Example 67 | 6/10 |

(b) Prostaglandin (PGE) Antagonism Assay

In order to determine the effectiveness of several of the compounds of the present invention ("test compounds") as prostaglandin $E_2$ antagonists, a prostaglandin antagonism assay was conducted, as described below, to determine the ability of these compounds to inhibit prostaglandin $E_2$-induced contractions of segments of guinea pig ileum. If a test compound inhibits prostaglandin $E_2$-induced contractions, it suggests that the compound functionally antagonizes prostaglandin $E_2$.

Male albino guinea pigs weighing 200 to 500 grams were sacrificed by cervical dislocation. The ilea were then quickly removed from the guinea pigs and placed in a modified Tyrode solution, a solution which is known to those skilled in the art, containing one-half of the usual amount of magnesium ions.

Segments of ileum about 2 cm long were then cut and mounted in a 10-mL tissue bath containing the modified Tyrode solution. The solution was maintained at 37° C. and aerated with a gaseous mixture of 95% oxygen and 5% carbon dioxide. Data for a control prostaglandin $E_2$ dose response curve plotting concentration of prostaglandin E versus the intensity of contractions, detected isotonically, was then obtained by experimentally adjusting the dose of the prostaglandin $E_2$ being injected into the tissue bath, in a manner known by those of skill in the art.

Solutions or suspensions containing an initial concentration (3 micromolar) of a test compound in modified Tyrode solution ("test solutions/suspensions") were then separately substituted for the control bath solution. Each test solution/suspension was then kept in constant contact with the ileum tissue, except for brief periods to drain the bath in preparation for rinsing with fresh test solution/suspension. A second prostaglandin $E_2$ dose response curve was then generated for prostaglandin $E_2$ in the presence of a test compound.

A dose ratio (DR) of $EC_{50}$ doses was then calculated from the results of each test in a manner known by those of skill in the art. A control dose response curve (DRC) is produced in isolated segments of guinea pig ileum mounted in an automated apparatus with six concentrations of prostaglandin $E_2$. A solution or suspension of test compound is substituted for the control bathing solution and is incubated for thirty minutes. An additional prostaglandin $E_2$ dose response curve is produced in the presence of the test compound. A dose ratio is calculated from the $EC_{50}$ values obtained from duplicate replications on each concentration of the test compound. A concentration of test compound is judged to be active if it produces a dose ratio significantly greater than that obtained in a series of blank treatments.

The results of this prostaglandin antagonism assay are presented in Table 2 below in terms of their dose ratio. The compounds of the present invention which were tested in this assay, and for which results are presented in Table 2, correspond to the particular examples specified in Table 2.

TABLE 2

Data Generated from the Prostaglandin Antagonism Assay

| Compound Tested | Dose Ratio |
|---|---|
| Example 3 | 1.5 |
| Example 5 | 2.4 |
| Example 7 | 5.1 |
| Example 9 | 1.4 |
| Example 13 | 1.6 |
| Example 15 | 2.1 |
| Example 17 | 3.1 |
| Example 19 | 6.0 |
| Example 20 | 8.0 |
| Example 22 | 3.0 |
| Exmaple 24 | 11.9 |
| Example 25 | 1.6 |
| Example 29 | 2.2 |
| Example 33 | 6.7 |
| Example 35 | 1.0 |
| Example 40 | 4.1 |
| Example 41 | 2.6 |
| Example 43 | 0.8 |
| Example 47 | 2.9 |
| Example 50 | 2.7 |
| Example 54 | 2.4 |
| Example 56 | 3.3 |
| Example 58 | 6.6 |
| Example 61 | 4.8 |
| Example 65 | 8.4 |
| Example 67 | 10.2 |
| Example 79 | 10 |
| Compound 81 | 32 |

While the present invention has been described herein with some specificity, and with reference to certain preferred embodiments thereof, those of ordinary skill in the art will recognize numerous variations, modifications and substitutions of that which has been described which can be made, and which are within the scope and spirit of the invention. For example, effective dosages other than the preferred ranges set forth hereinabove may be applicable as a consequence of variations in the responsiveness of the animal being treated, dosage-related adverse effects, if any, and analogous considerations. Likewise, the specific pharmacological responses observed may vary according to, and depending upon, the particular active compound selected, or whether there are present certain pharmaceutical carriers, as well as the type of formulation and mode of administration employed. Such expected variations and/or differences in the results are contemplated in accordance with the objects and practices of the present invention. It is intended therefore that all of these modifications and variations be within the scope of the present invention as described and claimed herein, and that the invention be limited only by the scope of the claims which follow, and that such claims be interpreted as broadly as is reasonable.

What is claimed is:

1. A compound having a structure:

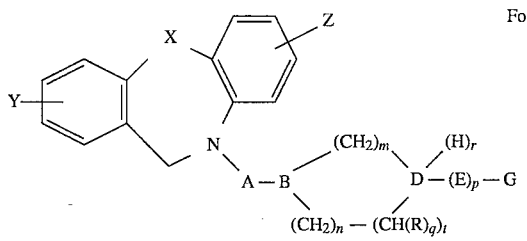

Formula I or a pharmaceutically-acceptable salt thereof, wherein:

X is oxygen, sulfur,

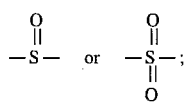

Y is hydrogen, halogen or hydroxy;

Z is hydrogen or halogen;

A is alkylene or carbonyl;

B is —CH or nitrogen;

D is carbon or nitrogen;

E is alkylene, carbonyl, alkyleneamino or alkylenecarbonyl;

G is hydrogen, alkyl, cycloalkyl, alkoxy, aminoalkyl, aminocycloalkyl, aryl, alkylenearyl or aryl-substituted aryl;

R is hydrogen or —$CO_2R^1$;

$R^1$ is hydrogen or alkyl;

m is an integer of from 0 to 4;

n is an integer of from 0 to 4;

r is 0 or 1;

q is an integer of from 0 to 1;

t is an integer of from 0 to 1; and p is an integer of from 0 to 1;

with the proviso that B and D cannot both be —CH, with the proviso that B cannot be —CH when G is hydrogen, alkyl or cycloalkyl, with the proviso that m and n are not each 0, with the proviso that G is not alkyl or cycloalkyl when X is sulfur, A is alkylene, B is —CH and D is nitrogen, with the proviso that G is not aminoalkyl or aminocycloalkyl when X is oxygen or sulfur, A is alkylene, B is nitrogen, R is hydrogen, D is carbon and r is 1;

with the proviso that G is not hydrogen or alkyl when X is oxygen or sulfur, A is alkylene, B is nitrogen, D is carbon, E is alkylene and f is 0 or 1; and with the proviso that G is not hydrogen, alkyl or cycloalkyl when X is oxygen or sulfur, A is carbonyl, B is nitrogen, E is alkylene and p is 0 or 1; and with the proviso that when q is 0 and t is 1, then the bond between the CH and D groups is a double bond.

2. A compound of claim 1 wherein X is oxygen.

3. A compound of claim 2 wherein Y is hydrogen.

4. A compound of claim 3 wherein A is carbonyl.

5. A compound of claim 4 wherein B is nitrogen.

6. A compound of claim 5 wherein R is —$CO_2R^1$, q is 1 and t is 1.

7. A compound of claim 6 wherein $R^1$ is alkyl.

8. A compound of claim 5 wherein R is —$CO_2R^1$, q is 1 and t is 0.

9. A pharmaceutical composition comprising a pharmaceutically-acceptable carrier and a therapeutically-effective amount of a compound of claim 1.

10. A method for treating pain in an animal comprising administering to said animal a therapeutically-effective amount of a compound of claim 1.

11. A method for treating diseases in an animal which are responsive to prostaglandin-$E_2$ antagonists comprising administering to said animal a therapeutically-effective amount of a compound of claim 1.

* * * * *